United States Patent
Farokhzad et al.

(10) Patent No.: US 11,850,309 B2
(45) Date of Patent: Dec. 26, 2023

(54) CATIONIC MATERIALS AND FORMULATIONS FOR DRUG DELIVERY

(71) Applicant: The Brigham and Women's Hospital, Inc., Boston, MA (US)

(72) Inventors: Omid Farokhzad, Waban, MA (US); Jun Wu, Boston, MA (US); Lili Zhao, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 447 days.

(21) Appl. No.: 17/001,237

(22) Filed: Aug. 24, 2020

(65) Prior Publication Data
US 2021/0228493 A1 Jul. 29, 2021

Related U.S. Application Data

(60) Continuation of application No. 16/733,004, filed on Jan. 2, 2020, now abandoned, which is a division of
(Continued)

(51) Int. Cl.
*A61K 9/51* (2006.01)
*A61K 9/50* (2006.01)
(Continued)

(52) U.S. Cl.
CPC .......... *A61K 9/5153* (2013.01); *A61K 9/0019* (2013.01); *A61K 9/5073* (2013.01);
(Continued)

(58) Field of Classification Search
CPC . A61K 9/5153; A61K 9/0019; A61K 47/6937
See application file for complete search history.

(56) References Cited

U.S. PATENT DOCUMENTS

| 5,534,499 A | 7/1996 | Ansell |
| 5,820,873 A | 10/1998 | Choi |

(Continued)

FOREIGN PATENT DOCUMENTS

WO 2013056113 4/2013

OTHER PUBLICATIONS

Brahmachari, et al., "Single-walled nanotube/amphiphile hybrids for efficacious protein delivery: rational modification of dispersing agents", Angew Chem Intl Ed., 50:11243-7 (2011).
(Continued)

*Primary Examiner* — Carlos A Azpuru
(74) *Attorney, Agent, or Firm* — PABST PATENT GROUP LLP

(57) ABSTRACT

Cationic polymers are provided for delivering anionic active agents, preferably in the form or nanoparticles and other nanostructures. The polymer can be a polycation homopolymer or a copolymer containing a polycation block. The polycations and polycation containing polymers can contain dicarboxylic acid ester units and units of ($\alpha$-amino acid)-$\alpha$, $\omega$-alkylene diester units. The nanoparticles can contain high loadings of anionic active agents, with sustained release of the active agents. Methods of making the polycations and polycation containing polymers are provided. Methods of making the nanoparticles and formulating them for administration to an individual in need thereof are also provided.

18 Claims, 11 Drawing Sheets

Related U.S. Application Data application No. 16/033,040, filed on Jul. 11, 2018, now Pat. No. 10,525,013, which is a continuation of application No. 15/107,260, filed as application No. PCT/US2014/068820 on Dec. 5, 2014, now Pat. No. 10,022,334.

(60) Provisional application No. 61/920,303, filed on Dec. 23, 2013.

(51) Int. Cl.

| | | |
|---|---|---|
| *A61K 9/00* | (2006.01) | |
| *A61K 47/60* | (2017.01) | |
| *A61K 47/59* | (2017.01) | |
| *A61K 47/64* | (2017.01) | |
| *A61K 47/69* | (2017.01) | |
| *A61K 38/38* | (2006.01) | |
| *A61K 38/28* | (2006.01) | |
| *C08G 81/00* | (2006.01) | |

(52) U.S. Cl.
CPC .......... *A61K 9/5078* (2013.01); *A61K 9/5192* (2013.01); *A61K 38/28* (2013.01); *A61K 38/38* (2013.01); *A61K 38/385* (2013.01); *A61K 47/593* (2017.08); *A61K 47/60* (2017.08); *A61K 47/645* (2017.08); *A61K 47/6931* (2017.08); *A61K 47/6937* (2017.08); *C08G 81/00* (2013.01)

(56) References Cited

U.S. PATENT DOCUMENTS

| | | | |
|---|---|---|---|
| 5,885,613 A | 3/1999 | Holland | |
| 8,545,830 B2 | 10/2013 | Lowe | |
| 10,022,334 B2* | 7/2018 | Farokhzad | ........... A61K 47/593 |
| 2002/0044972 A1 | 4/2002 | Davis | |
| 2010/0022680 A1 | 1/2010 | Karnik | |
| 2011/0065208 A1 | 3/2011 | Boriss | |
| 2011/0065807 A1* | 3/2011 | Radovic-Moreno | ..... A61K 9/51 514/772.3 |
| 2012/0135054 A1 | 5/2012 | Chu | |
| 2013/0109743 A1 | 5/2013 | Kataoka | |

OTHER PUBLICATIONS

Caryalho, et al., "Formulations for pulmonary administration of anticancer agents to treat lung malignancies", J Aerosol Med Pulm Drug Deliv., 24(2):61-80 (2011).

Duncan, "The dawning era of polymer therapeutics", Nat Rev Drug Discov., 2(5):347-60 (2003).

Duncan, et al, "Polymer therapeutics—polymers as drugs, drug and protein conjugates and gene delivery systems: past, present and future opportunities", J Drug Target., 14:337-41 (2006).

Gu, et al., "Tailoring nanocarriers for intracellular protein delivery", Chem. Soc. Rev., 40:3638-55 (2011).

International Search Report for corresponding PCT application PCT/US2014/068820 dated Feb. 13, 2015.

Kamaly, et al, "Development and in vivo efficacy of targeted polymeric inflammation-resolving nanoparticles", PNAS, 110:6506-11 (2013).

Kang, et al, "Nanoscaled buffering zone of charged (PLGA)n-b-bPEI micelles in acidic microclimate for potential protein delivery application.", J. Controlled Rel., 160:440-50 (2012).

Langer, et al, "Polymers for the sustained release of proteins and other macromolecules", Nature, 263:797-800 (1976).

Peppas, et al, "Hydrogels for oral delivery of therapeutic proteins", Expert Opin Biol Ther., 4:881-7 (2004).

Rana, et al, "Engineering the nanoparticle-protein interface: applications and possibilities", Curr Opin Chem Biol., 14:828-34 (2010).

Swaminathan, et al., "Liposomal delivery of proteins and peptides", Expert Opin Drug Deliv., 9:1489-503 (2012).

Vermonden, et al, "Hydrogels for protein delivery", Chem. Rev., 112:2853-88 (2012).

Wang, et al,, "Co-delivery of drugs and DNA from cationic core-shell nanoparticles self-assembled from a biodegradable copolymer", Nat Mater., 5(10):791-6 (2006).

Wu, et al., "Biodegradable arginine-based poly(ether ester amide)s as a non-viral DNA delivery vector and their structure-function study", J. Mat. Chem., 22: 18983-91 (2012b).

Wu, et al., "Cationic Hybrid Hydrogels from Amino-Acid-Based Poly(ester amide): Fabrication, Characterization, and Biological Properties", Adv.Func. Mat., 22(18):3815-23 (2012).

Yan, et al, "Recent advances in liposome-based nanoparticles for antigen delivery.", Polymer Reviews, 47:329-44 (2007).

* cited by examiner

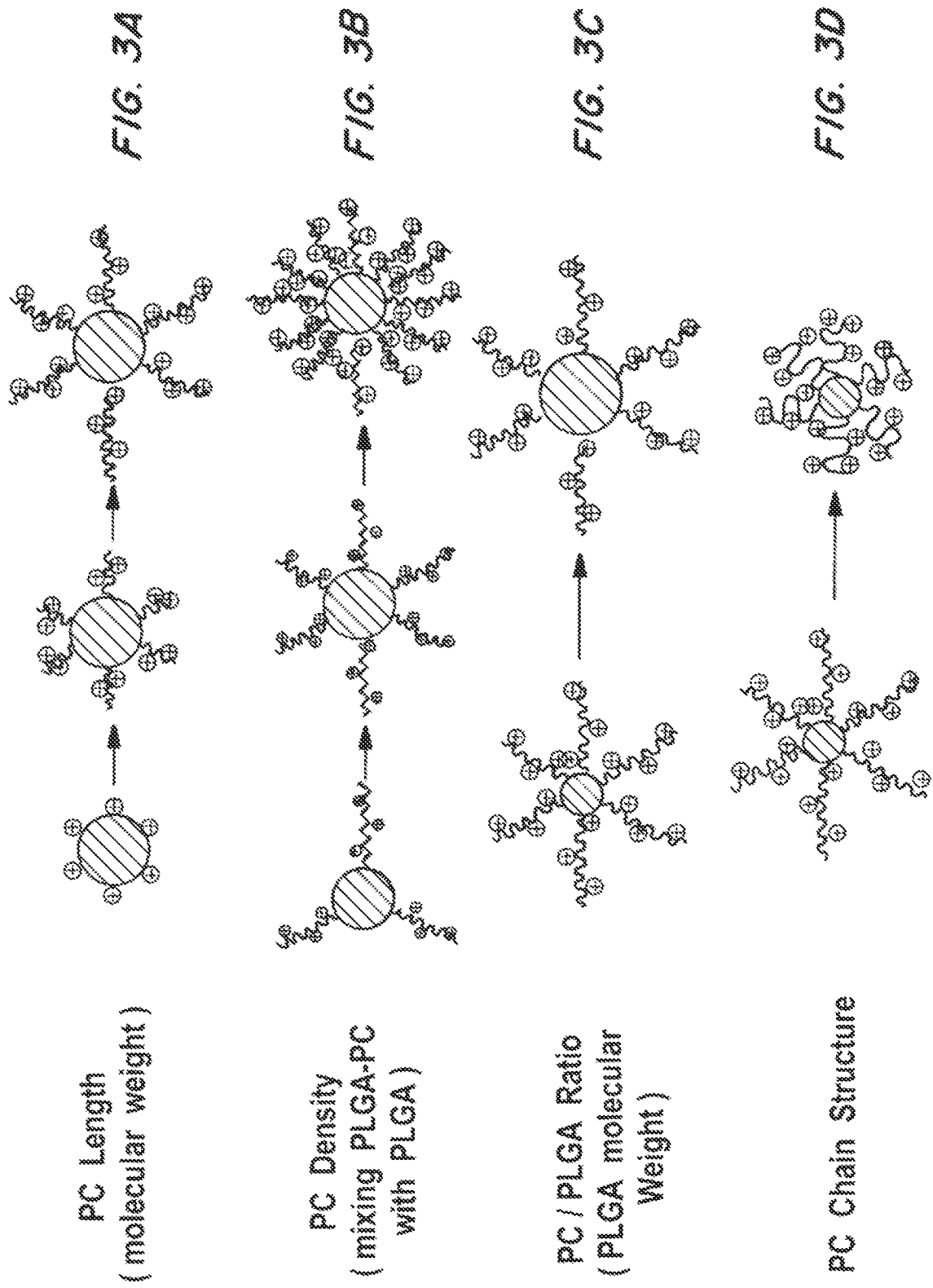

Lipid

Lipid-PEG    PLGA    PLGA-PEG

CATIONIC MATERIALS AND FORMULATIONS FOR DRUG DELIVERY

CROSS-REFERENCE TO RELATED APPLICATIONS

This application is a continuation of U.S. application Ser. No. 16/733,004 filed Jan. 2, 2020, which is a divisional of U.S. application Ser. No. 16/033,040 filed Jul. 11, 2018, now U.S. Patent No. 10,525,013, issued Jan. 7, 2020, which is a continuation of U.S. application Ser. No. 15/107,260 filed Jun. 22, 2016, now U.S. Pat. No. 10,022,334, issued Jul. 17, 2018, which is a National Phase application under 35 U.S.C. § 371 of International Application No. PCT/US2014/068820, filed Dec. 5, 2014, which claims benefit of and priority to U.S. Provisional Application No. 61/920,303, filed Dec. 23, 2013, all of which are hereby incorporated herein by reference in their entirety.

STATEMENT REGARDING FEDERALLY SPONSORED RESEARCH OR DEVELOPMENT

This invention was made with government support under grant number CA151884 and grant number EB015419-01 awarded by the National Institutes of Health. The government has certain rights in the invention.

FIELD OF THE INVENTION

This invention is generally in the field of materials for pharmaceutical applications.

BACKGROUND OF THE INVENTION

The delivery of any therapeutic compound to an individual or a patient in need thereof may be impeded by any one or several factors such as limited ability of the compound to reach a target cell or tissue, or by restricted entry or trafficking of the compound within cells. Various delivery vectors have been developed to encapsulate and deliver many classes of drugs and have proven a promising strategy to effectively treat cancers, diabetes, cardiovascular diseases, and many other disorders. For anionic drugs, such as proteins and nucleic acids, safe and effective delivery to the desired disease locations or intracellular sites remains a major challenge. This is, at least in part, due to the intrinsic properties of these drugs. Most proteins have high molecular weight (MW), surface charges, and/or vulnerable tertiary structures (Gu et al, *Chem. Soc. Rev.* 2011, 40:3638). Nucleic acids have the similar issues. Many nucleic acids are stable for only limited times in cells or plasma. Nucleic acid drugs should usually be delivered into the corresponding intracellular target site, i.e. the nucleus or cytosol. Specific and robust delivery vehicles are needed to facilitate loading, delivery, and controlled release of anionic drugs, especially for proteins and nucleic acids.

Numerous platforms have been developed as carriers of anionic proteins, and nucleic acids. Microspheres (Langer et al, *Nature* 1976, 263: 797; Kang et al, *J. Controlled Rel.* 2012, 160: 440) and hydrogels (Vermonden et al, *Chem. Rev.* 2012, 112: 2853; Peppas et al, K, *Expert Opinion on Biological Therapy* 2004, 4: 881) have been utilized to solve the sustained protein and nucleic acid release issue. These systems have limited applications for intracellular protein and nucleic acid delivery due to their large size. Platforms such as liposomes (Swaminathan et al, *Expert Opinion on Drug Delivery* 2012, 9:1489; Yan et al, *Polymer Reviews* 2007, 47:329.), conjugates (Duncan et al, Journal of Drug Targeting 2006, 14:337; Duncan, *Nat Rev Drug Discov* 2003, 2:347), nanotubes (Brahmachari et al, *Angewandte Chemie International Edition* 2011, 50:11243), and polymeric nanoparticles (Kamaly et al, *PNAS* 2013, 110:6506; Rana et al, *Current Opinion in Chemical Biology* 2010, 14:828) are being extensively investigated for effective intracellular delivery. These platforms often suffer from low loading of the negatively charged drug and release profiles characterized by a large initial burst release.

The anionic proteins, anionic protein analogues and nucleic acids are negatively charged and have complicated, sensitive, and fragile 3-D structure with nm scale sizes. There remains a need for materials and methods to load and encapsulate proteins and nucleic acids with high efficiency and high loading, and release them in a sustained manner while maintaining their bioactivity.

It is therefore an object of the invention to provide improved materials, compositions, and formulations for drug delivery, especially of negatively charged drugs such as proteins and nucleic acids.

It is an additional object of the invention to provide compositions with high loading efficiency of negatively charged drugs such as proteins and nucleic acids.

It is also an object of the invention to provide compositions with sustained release of active agents, including sustained release of negatively charged drugs such as proteins and nucleic acids.

It is a further object of the invention to provide methods of making improved materials, compositions, and formulations for drug delivery, especially of negatively charged drugs such as proteins and nucleic acids.

It is additionally an object of the invention to provide methods of using the materials, compositions, and formulations to delivery negatively charged drugs to a patient in need thereof.

SUMMARY OF THE INVENTION

Cationic polymers are provided for drug delivery. The cationic polymers can be used for delivering anionic active agents, preferably in the form of nanoparticles and other nanostructures. In some embodiments the nanoparticles and nanostructures have high loading efficiencies, even for anionic active agents such as nucleic acids and negatively charged proteins. Methods of making the polymers, nanoparticles containing the polymers, and pharmaceutical formulations thereof are also provided. Methods of using the nanoparticles and the pharmaceutical formulations drug delivery, including for the delivery of anionic active agents to a patient in need thereof are also provided. The delivery systems allows co-loading and delivery of multiple drugs, and, responsive release at desired time points or sites.

The polymer can be a polycation homopolymer or a copolymer containing a polycation block. In some embodiments the polycation is positively charged in neutral, acidic, and most basic pH environments. The polymer can be a block copolymer such as a di-block, tri-block or other multi-block copolymer including a polycation block with additional polymer blocks that can include hydrophilic polymers, hydrophobic polymers, biodegradable polymers, or a combination thereof. The block copolymer can be an amphiphilic polymer. The polycation or polycation containing copolymer can be a low molecular weight polymer, e.g. having a molecular weight between 100 Da 10 kDa or between 1.0 kDa and 10.0 kDa, or can be a high molecular weight polymer, e.g having a molecular weight between 40 kDa and 60 kDa or between 40 kDa and 1,000 kDa.

The polycations and polycation containing polymers provided can contain dicarboxylic acid ester units and units of (α-amino acid)-α,ω-alkylene diester units. The (α-amino acid)-α,ω-alkylene diester units can include cationic amino acids such as lysine, arginine and histidine. The dicarboxylic acid ester can include dicarboxylic acids of linear and branched alkyl and substituted alkyl, alkenyl, or alkylene oxide containing from 2 to 20 carbon atoms. The polycation can contain units having the structure

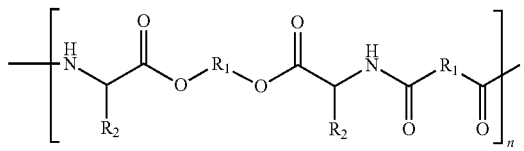

where the $R_1$ groups include linear and branched alkyl and substituted alkyl, alkenyl, or alkylene oxide containing from 2 to 20 carbon atoms; at least one $R_2$ is a cationic hydrophilic side chain containing from 1 to 12 carbon atoms. In some embodiments $R_2$ can be aliphatic amine, cycloaliphatic amine, heterocyclic amine or aromatic amine, provided that there is at least one positively charged amine group in the side chain. $R_2$ can be the side chain of cationic amino acids such as lysine, arginine and histidine.

Core shell and multi-core shell nanoparticles are provided. The core-shell and multi-core shell nanoparticles can contain the polycations and/or the polycation containing polymers. The core-shell and multi-core shell nanoparticles can contain inorganic particles. The core shell and multi-core shell particles can contain additional polymers such as hydrophilic polymers, hydrophobic polymers, biodegradable polymers, or a combination thereof. In some embodiments one or more of the polymers are amphiphilic. In some embodiments the nanoparticles have a diameter between 50 nm and 350 nm or between 10 nm and 1,000 nm.

The nanoparticles can contain one or more cationic particle cores containing a polycation or a polycation containing polymer. In preferred embodiments the cationic polymer core contains a block copolymer having a hydrophobic polymer block and a hydrophilic polycation block, e.g. a polylactic-co-glycolic) acid-b-Polycation (PLGA-PC) block copolymer. The cationic particle core can contain a second polymer containing the hydrophobic polymer without the polycation block. For example, the cationic particle core can contain a PLGA-PC block copolymer and a PLGA homopolymer.

In some embodiments the core-shell nanoparticles can contain an outer layer physically attached or chemically conjugated. The outer layer can include one or more of a biodegradable polymer, a stealth polymer, a lipid, a surfactant, amphiphilic polymer, or a polymer-lipid conjugate. Exemplary embodiments provide a core-shell nanoparticle having (1) a cationic particle core; (2) an outer protective layer; and (3) a layer or shell or multiple layers of anionic active agent dispersed between the cationic particle core and the protective layer. In some embodiments the core-shell nanoparticle is a multi-core shell nanoparticle containing more than one cationic particle core encapsulated by and dispersed within a plurality of anionic active agents.

Formulations a contain an effective amount of the particles for administration to an individual in need thereof. The formulation can be parenteral formulations. The formulations can be injectable formulations, e.g., solutions or suspensions; solid forms suitable for preparing solutions or suspensions upon the addition of a reconstitution medium prior to injection; emulsions, e.g. water-in-oil (w/o) emulsions, oil-in-water (o/w) emulsions, and microemulsions thereof, liposomes, or emulsomes.

Methods of making the polycations and polycation containing polymers are provided. In preferred embodiments the method includes the polycondensation reaction of a bis-(α-amino acid) diester with a di-acid or the activated ester thereof. The di-acid can be succinic acid, adipic acid, or sebacic acid. Methods of making and formulating the nanoparticles are also provided.

The formulations are useful for intracellular delivery, as well as extracellular delivery and systemic delivery to a body or regional delivery to an organ or tissue.

BRIEF DESCRIPTION OF THE DRAWINGS

FIGS. 3A-3D depict some of the parameters that can be adjusted to alter the particle properties including, polycation chain length/molecular weight (3A); ratio of PLGA-PC polymer to PLGA polymer (3B); PC:PLGA ratio/PLGA molecular weight (3C); and structure of the polycation (3D).

DETAILED DESCRIPTION OF THE INVENTION

Figure 1:
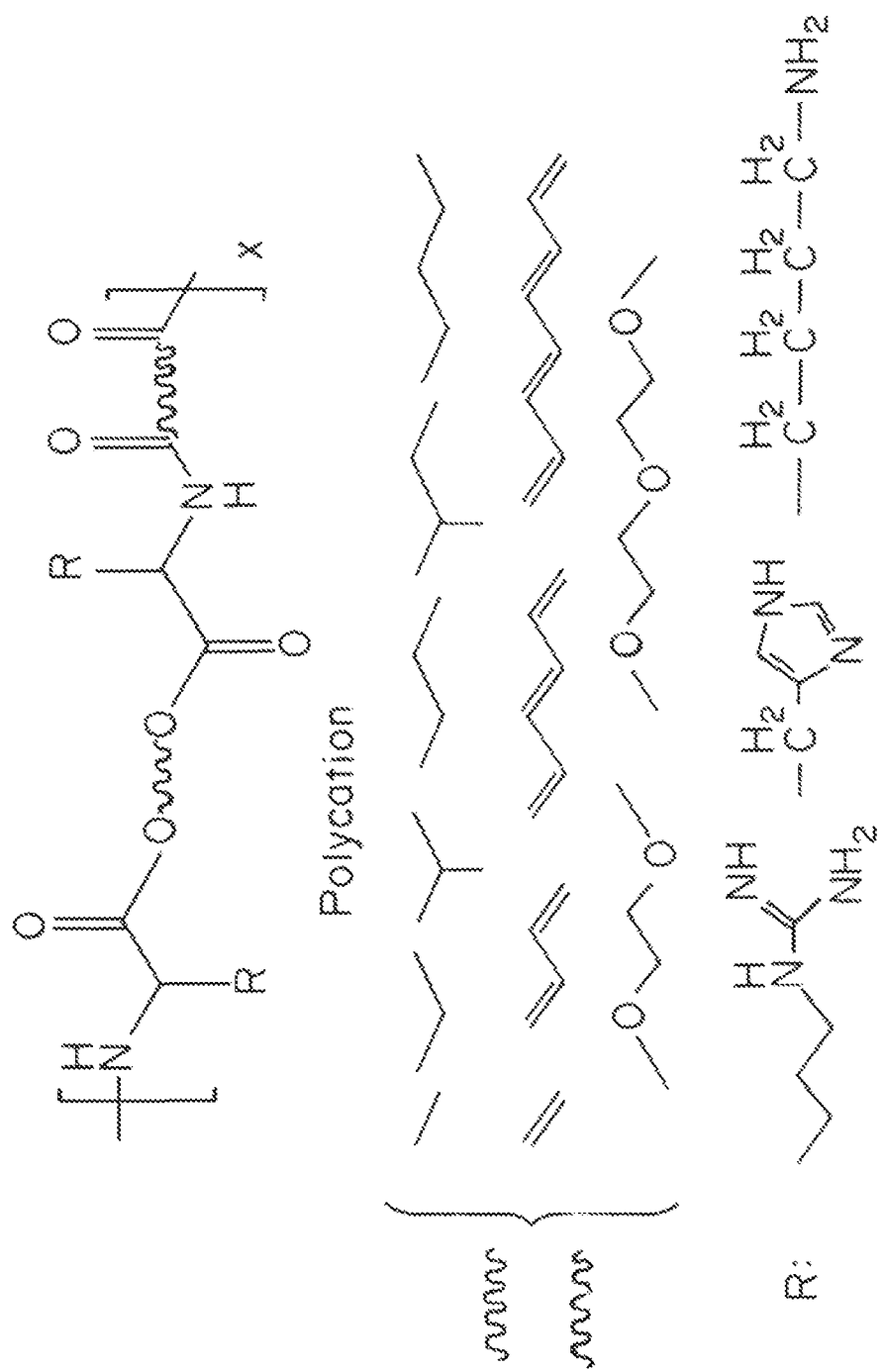
FIG. 1 depicts the structure of some exemplary polycations containing arginine, lysine, or histidine side chains.
Figure 2:
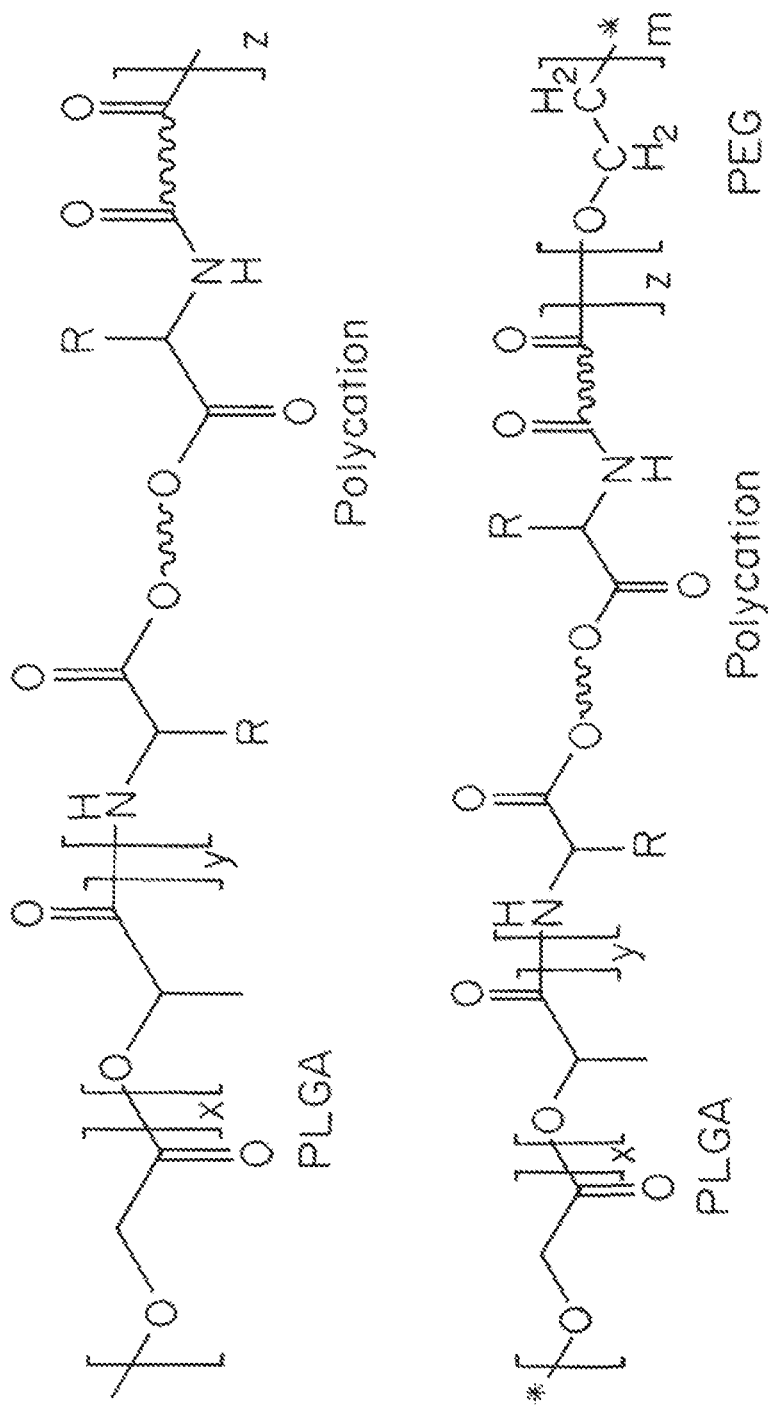
FIG. 2 depicts the structure of an exemplary PLGA-PC block copolymer (top) and a PLGA-PC-PEG block copolymer (bottom).

A polymeric nanoparticle platform is provided for delivery of negatively charged active agents such as proteins and nucleic acids. The nanoparticles can exhibit one or more of: (1) high loading efficiency thereby reducing required nanoparticle mass to achieve therapeutic dose; (2) no or limited organic solvents used during formulation to prevent denaturation; (3) minimal contact with carriers to avoid unwanted interactions or relatively low local pH environment caused by polymer degradation; and (4) sustainable and controllable release with low initial burst.

I. Definitions

The terms "subject" or "patient", as used herein, refer to any organism to which the particles may be administered, e.g. for experimental, therapeutic, diagnostic, and/or prophylactic purposes. Typical subjects include animals (e.g., mammals such as mice, rats, rabbits, non-human primates, and humans) and/or plants.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "altered level of expression" of a marker, protein or gene refers to an expression level in a test sample (e.g., a sample derived from a subject during or following treatment for a metabolic disorder, such as diabetes and/or obesity), that is greater or less than the standard error of the assay employed to assess expression and may be at least two, five, s ten times, 100, 500 or 1000 times the expression level in a control sample (e.g., a sample from the subject prior to treatment), or the average expression level of the marker in several control samples.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

"Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.
Transdermal "Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The terms "sufficient" and "effective", as used interchangeably herein, refer to an amount (e.g. mass, volume, dosage, concentration, and/or time period) needed to achieve one or more desired result(s). A "therapeutically effective amount" is at least the minimum concentration required to effect a measurable improvement or prevention of any symptom or a particular condition or disorder, to effect a measurable enhancement of life expectancy, or to generally improve patient quality of life. The therapeutically effective amount is thus dependent upon the specific biologically active molecule and the specific condition or disorder to be treated. Therapeutically effective amounts of many active agents, such as antibodies, are well known in the art. The therapeutically effective amounts of anionic proteins, protein analogues, or nucleic acids hereinafter discovered or for treating specific disorders with known proteins, protein analogues, or nucleic acids to treat additional disorders may be determined by standard techniques which are well within the craft of a skilled artisan, such as a physician.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

The term "prodrug" refers to an agent, including nucleic acids and proteins, which is converted into a biologically active form in vitro and/or in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. *Progress in Drug Research*, 4:221-294; Morozowich et al. (1977). Application of Physical Organic Principles to Prodrug Design in E. B. Roche ed. *Design of Biopharmaceutical Properties through Prodrugs and Analogs*, APhA; Acad. Pharm. Sci.; E. B. Roche, ed. (1977). *Bioreversible Carriers in Drug in Drug Design, Theory and Application*, APhA; H. Bundgaard, ed. (1985) *Design of Prodrugs*, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, *Eds., Transport Processes in Pharmaceutical Systems*, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3):183-209; Browne (1997). Fosphenytoin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) *Design of Prodrugs*, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.*, 72(3): 324-325; Han, H. K. et al. (2000). Targeted prodrug design to optimize drug delivery, *AAPS PharmSci.*, 2(1): E6; Sadzuka Y. (2000). Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl. 2:S15-27; Wang, W. et al. (1999) Prodrug approaches to the improved delivery of peptide drugs. *Curr. Pharm. Des.*, 5(4):265-87.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties. "Amphiphilic material" as used herein refers to a material containing a hydrophobic or more hydrophobic oligomer or polymer (e.g., biodegradable oligomer or polymer) and a hydrophilic or more hydrophilic oligomer or polymer.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation.

Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyryl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

The term "activated ester", as used herein, refers to alkyl esters of carboxylic acids where the alkyl is a good leaving group rendering the carbonyl susceptible to nucleophilic attack by molecules bearing amino groups. Activated esters are therefore susceptible to aminolysis and react with amines to form amides. Activated esters contain a carboxylic acid ester group —CO$_2$R where R is the leaving group.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 100 or fewer such as 30 or fewer carbon atoms in its backbone (e.g., $C_1$-$C_{100}$ for straight chains, $C_3$-$C_{100}$ for branched chains), preferably 50 or fewer, more preferably 25 or fewer, most preferably 12 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

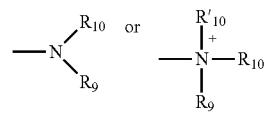

wherein $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

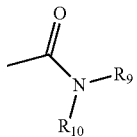

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or nonaromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "carbonyl" is art-recognized and includes such moieties as can be represented by the general formula:

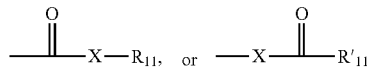

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_H$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "mean particle size", as used herein, generally refers to the statistical mean particle size (diameter) of the particles in the composition. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering. Two populations can be said to have a "substantially equivalent mean particle size" when the statistical mean particle size of the first population of nanoparticles is within 20% of the statistical mean particle size of the second population of nanoparticles; more preferably within 15%, most preferably within 10%.

The terms "monodisperse" and "homogeneous size distribution", as used interchangeably herein, describe a population of particles, microparticles, or nanoparticles all having the same or nearly the same size. As used herein, a monodisperse distribution refers to particle distributions in which 90% of the distribution lies within 5% of the mean particle size. The terms "polypeptide," "peptide" and "protein" generally refer to a polymer of amino acid residues. As used herein, the term also applies to amino acid polymers in which one or more amino acids are chemical analogues or modified derivatives of corresponding naturally-occurring amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

The terms "nucleic acid," "polynucleotide," and "oligonucleotide" are used interchangeably to refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general and unless otherwise specified, an analogue of a particular nucleotide has the same base-pairing specificity; i.e., an analogue of A will base-pair with T. The term "nucleic acid" is a term of art that refers to a string of at least two base-sugar-phosphate monomeric units. Nucleotides are the monomeric units of nucleic acid polymers. The term includes deoxyribonucleic acid (DNA) and ribonucleic acid (RNA) in the form of a messenger RNA, anti-sense, plasmid DNA, parts of a plasmid DNA or genetic material derived from a virus. Anti-sense is a polynucleotide that interferes with the function of DNA and/or RNA. The term nucleic acids-refers to a string of at least two base-sugar-phosphate combinations. Natural nucleic acids have a phosphate backbone, artificial nucleic acids may contain other types of backbones, but contain the same bases. The term also includes PNAs (peptide nucleic acids), phosphorothioates, and other variants of the phosphate backbone of native nucleic acids.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

II. Polymers

Cationic polymers are provided for delivering anionic active agents, e.g in the form or nanoparticles and other nanostructures, or other pharmaceutical formulations. The polymers can be homopolymers or copolymers containing a cationic polymer block. The polymers can be biocompatible and/or biodegradable in whole or in part. The polymer may have any molecular weight adjusted dependent upon the specific application. The polymer can have a molecular weight between 100 Da and 10,000 kDa, between 100 Da and 1,000 kDa, between 1.0 kDa, and 500 kDa, or between 3.0 kDa and 100 kDa.

In some embodiments the polymer is a low molecular weight polymer, e.g. less than 20.0 kDa, less than 15 kDa, less than 12 kDa, or less than 10 kDa. The polymers can have a molecular weight between 1.0 kDa and 20.0 kDa, e.g. between 1.0 kDa and 12.0 kDa, between 1.0 kDa and 6.0 kDa, between 2.0 kDa and 5.0 kDa, between 3.0 kDa and 4.5 kDa, between 3.5 kDa and 4.0 kDa, between 7.0 kDa and 11.0 kDa, between 8.0 kDa and 11.0 kDa, between 8.5 kDa and 9.0 kDa, or between 9.0 kDa and 10.0 kDa.

In alternative embodiments the polymer is a high molecular weight polymer, e.g. greater than 20 kDa, greater than 30 kDa, or greater than 40 kDa.

The polymer can have a molecular weight between 40 kDa and 60 kDa, between 45 kDa and 60 kDa, between 45 kDa and 50 kDa, between 48 kDa and 49 kDa, between 50 kDa and 60 kDa, or between 50 kDa and 55 kDa.

A. Polycation Polymers

The polymers can be polycations or can be copolymers that include one or more polycation blocks. The polycation can contain one or more cationic amino acids or amino acid derivatives. The polycation is preferably positively charged at a physiological pH. The polycation can be positively charged at neutral and acidic environments. In some embodiments the polycation is positively charged even in most basic pH environments. The polycation will generally be positively charged at a pH superior to the pKa. The polycation can have a pKa greater than 5.0, greater than 7.0, greater than 9.0, greater than 11.0, greater than 11.5, greater than 12.0, or greater than 12.5. In some embodiments the polycation has a pKa between 5.0 and 12.5, between 5.0 and 10.5, between 5.0 and 9.0, or between 6.0 and 8.0.

The polycation or polycation block may have any molecular weight from about 100 Da to about 10,000 kDa. The polycation polymer or polycation block can have a molecular weight less than 1,000 kDa, less than 100 kDa, less than 30 kDa, less than 20 kDa, less than 15 kDa, less than 12 kDa, or less than 6 kDa.

The polycation can contain dicarboxylic acid ester units and units of amino acids diesters. The amino acids can be $\alpha$, $\beta$, $\gamma$, $\delta$, or $\varepsilon$ amino acids. In preferred embodiments the polycation contains dicarboxylic acid ester units and ($\alpha$-amino acid)-$\alpha,\omega$-alkylene diester units. The polycation can contain 1, 2, 3, or more different types of dicarboxylic acid ester units or amino acid diester units. In some embodiments the polycation contains only a single type of dicarboxylic acid ester unit, only a single type of amino acid diester units, or both. The molar ratio of dicarobylic acid ester units to ($\alpha$-amino acid)-$\alpha,\omega$-alkylene diester units can be 1 to 1, can be less than 1, or can be greater than 1. In preferred embodiments the molar ratio of dicarboxylic acid ester units to ($\alpha$-amino acid)-$\alpha,\omega$-alkylene diester units is between 2:5 and 1:1, is between 1:2 and 1:1, or is between 3:5 and 9:10. The ratios can be adjusted to achieve polycations with different end groups.

The ($\alpha$-amino acid)-$\alpha,\omega$-alkylene diester units include amino acids that are preferably positively charged at a physiological pH. The ($\alpha$-amino acid)-$\alpha,\omega$-alkylene diester units can include amino acids that are positively charged at neutral and acidic pH, and in some cases are positively charged at some basic pH. The ($\alpha$-amino acid)-$\alpha,\omega$-alkylene diester units can include cationic amino acids such as lysine, arginine and histidine as well as analogues thereof such as homolysine, ornithine, diaminobutyric acid, diaminopimelic acid, diaminopropionic acid and homoarginine as well as trimethyllysine and trimethylornithine, 4-aminopiperidine-4-carboxylic acid, 4-amino-1-carbamimidoylpiperidine-4-carboxylic acid and 4-guanidinophenylalanine. In some embodiments the ($\alpha$-amino acid)-$\alpha,\omega$-alkylene diester units do not include arginine. In some embodiments the ($\alpha$-amino acid)-$\alpha,\omega$-alkylene diester units do not include lysine. The ($\alpha$-amino acid)-$\alpha,\omega$-alkylene diester units can include cationic amino acid groups having a pKa greater than 5.0, greater than 7.0, greater than 9.0, greater than 11.0, greater than 11.5, greater than 12.0, or greater than 12.5. In some embodiments the $\alpha$-amino acid)-$\alpha,\omega$-alkylene diester units can include cationic amino acid groups having a pKa between 5.0 and 12.5, between 5.0 and 10.5, between 5.0 and 9.0, or between 6.0 and 8.0.

The dicarobylic acid ester units can have the structure

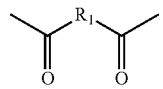

where $R_1$ is a substituted or unsubstituted alkyl, alkenyl, alkynyl, cycloalkyl, heterocycloalkyl, cycloalkenyl, heterocycloalkenyl, aryl, or heteroaryl. In some embodiments $R_1$ is a substituted or unsubstituted alkyl, alkenyl, alkynyl, cycloalkyl, heterocycloalkyl, cycloalkenyl, heterocycloalkenyl, aryl, or heteroaryl containing from 1 to 100 carbon atoms, from 1 to 30 carbon atoms, from 1 to 20 carbon atoms, from 1 to 12 carbon atoms, or from 2 to 10 carbon atoms. $R_1$ can be a linear or branched alkyl, substituted alkyl, alkenyl, substituted alkenyl, alkylene oxide, or substituted alkylene oxide. Exemplary $R_1$ groups include linear and branched alkyl and substituted alkyl, alkenyl, or alkylene oxide containing from 2 to 20, preferably from 2 to 12 carbon atoms.

The polycation can include (α-amino acid)-α,ω-alkylene diester having the structure

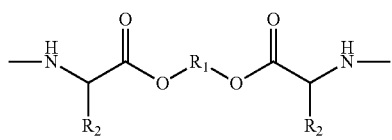

where $R_1$ is a substituted or unsubstituted alkyl, alkenyl, alkynyl, cycloalkyl, heterocycloalkyl, cycloalkenyl, heterocycloalkenyl, aryl, or heteroaryl; and $R_2$ is a linear or branched alkyl, alkenyl, cycloalkyl, heterocycloalkyl, cycloalkenyl, heterocycloalkenyl, aryl, or heteroaryl group at least one of which is substituted with one or more cationic primary, secondary, or tertiary amino groups or quaternary ammonium, sulfonium or phosphinium groups. In some embodiments $R_1$ is a substituted or unsubstituted alkyl, alkenyl, alkynyl, cycloalkyl, heterocycloalkyl, cycloalkenyl, heterocycloalkenyl, aryl, or heteroaryl containing from 1 to 30 carbon atoms, from 1 to 20 carbon atoms, from 1 to 12 carbon atoms, or from 2 to 10 carbon atoms. $R_1$ can be a linear or branched alkyl, substituted alkyl, alkenyl, substituted alkenyl, alkylene oxide, or substituted alkylene oxide. Exemplary $R_1$ groups include linear and branched alkyl and substituted alkyl, alkenyl, or alkylene oxide containing from 2 to 20, preferably from 2 to 12 carbon atoms. In preferred embodiments at least one $R_2$ is a cationic hydrophilic side chain containing from 1 to 12 carbon atoms. Each $R_2$ can independently be aliphatic amine, cycloaliphatic amine, heterocyclic amine or aromatic amine, provided that there is at least one positively charged amine group in the side chain. The positively charged amine group can have a pKa greater than 5.0, greater than 7.0, greater than 9.0, greater than 11.0, greater than 11.5, greater than 12.0, or greater than 12.5. In some embodiments the positively charged amine groups has a pKa between 5.0 and 12.5, between 5.0 and 10.5, between 5.0 and 9.0, or between 6.0 and 8.0. $R_2$ can be the side chain of cationic amino acids such as lysine, arginine and histidine, homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine. In some embodiments $R_2$ is not the side chain of arginine. In some embodiments $R_2$ is not the side chain of lysine. In some embodiments, when $R_2$ is a linear alkyl amine the linear alkyl group contains more than 4 carbon atoms.

The polycation or polycation block can include units having the structure

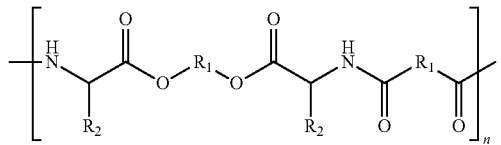

where each $R_1$ is independently a substituted or unsubstituted alkyl, alkenyl, alkynyl, cycloalkyl, heterocycloalkyl, cycloalkenyl, heterocycloalkenyl, aryl, or heteroaryl; each $R_2$ is independently a linear or branched alkyl, alkenyl, cycloalkyl, heterocycloalkyl, cycloalkenyl, heterocycloalkenyl, aryl, or heteroaryl group substituted with one or more cationic primary, secondary, or tertiary amino groups or quaternary ammonium, sulfonium or phosphinium groups; and n is any an integer less than about 10,000, preferably less than about 1,000, between 10 and 1,000, more preferably between 10 and 500. In some embodiments $R_1$ is a substituted or unsubstituted alkyl, alkenyl, alkynyl, cycloalkyl, heterocycloalkyl, cycloalkenyl, heterocycloalkenyl, aryl, or heteroaryl containing from 1 to 30 carbon atoms, from 1 to 20 carbon atoms, from 1 to 12 carbon atoms, or from 2 to 10 carbon atoms. $R_1$ can be a linear or branched alkyl, substituted alkyl, alkenyl, substituted alkenyl, alkylene oxide, or substituted alkylene oxide. Exemplary $R_1$ groups include linear and branched alkyl and substituted alkyl, alkenyl, oralkylene oxide containing from 2 to 20, preferably from 2 to 12 carbon atoms. In preferred embodiments $R_2$ is a cationic hydrophilic side chain containing from 1 to 12 carbon atoms. $R_2$ can be aliphatic amine, cycloaliphatic amine, heterocyclic amine or aromatic amine, provided that there is at least one positively charged amine group in the side chain. The positively charged amine group can have a pKa greater than 5.0, greater than 7.0, greater than 9.0, greater than 11.0, greater than 11.5, greater than 12.0, or greater than 12.5. In some embodiments the positively charged amine groups has a pKa between 5.0 and 12.5, between 5.0 and 10.5, between 5.0 and 9.0, or between 6.0 and 8.0. $R_2$ can be the side chain of cationic amino acids such as lysine, arginine and histidine, homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine. In some embodiments $R_2$ is not the side chain of arginine. In some embodiments $R_2$ is not the side chain of lysine. In some embodiments, when $R_2$ is a linear alkyl amine the linear alkyl group contains more than 4 carbon atoms.

B. Block Copolymers

The polymer can be a block copolymer such as a multi-block, e.g. di-block or a tri-block copolymer including a polycation block as described above with additional polymer blocks that can include hydrophilic polymers, hydrophobic polymers, biodegradable polymers, or a combination thereof. The block copolymer can be amphiphilic, can contain an amphiphilic polymer block, or both.

The block copolymer can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); or PLURONIC®, nonionic triblock copolymers composed of a central hydrophobic chain of polyoxypropylene (poly(propylene oxide)) flanked by two hydrophilic chains of polyoxyethylene (poly(ethylene oxide)), sold by BASF; poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), and copolymers thereof.

The block copolymer can contain one or more hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the block copolymer contains an aliphatic polyester. In preferred embodiments, the block copolymer contains poly(lactic acid), poly(glycolic acid), or poly(lactic acid-co-glycolic acid) blocks.

The block copolymer can contain one or more biodegradable polymers.

Biodegradable polymers can include polymers that are insoluble or sparingly soluble in water that are converted chemically or enzymatically in the body into water-soluble materials. Biodegradable polymers can include soluble polymers crosslinked by hydolyzable cross-linking groups to render the crosslinked polymer insoluble or sparingly soluble in water.

Biodegradable polymers in the block copolymer can include polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the block copolymer contains biodegradable polyesters or polyanhydrides such as poly(lactic acid), poly(glycolic acid), and poly(lactic-co-glycolic acid).

The block copolymers can have the structure X—PC, Y—PC, X—PC—Y, $(X-PC)_n$, $(X-PC)_n-Y$, $(X-PC-Y)_n$, or $X-(PC-Y)_n$ where PC is a polycation block, X is a hydrophobic polymer block, Y is a hydrophilic polymer block, and n is an integer from 2 to 10. One or more of the polycation block, the hydrophobic polymer block, or the hydrophilic polymer block can be biodegradable in whole or in part. In preferred embodiments X is an aliphatic polyester block such as poly(lactic acid), poly(glycolic acid), or poly(lactic acid-co-glycolic acid) having a molecular weight between 0.5 kDa and 500 kDa, preferably between 1 kDa and 100 kDa, preferably between 5 kDa and 50 kDa. In preferred embodiments Y is a hydrophilic polyalkylene glycol such as polyethylene glycol or polypropylene glycol having a molecular weight between 0.5 kDa and 500 kDa, preferably between 1 kDa and 50 kDa, preferably between 1 kDa and 20 kDa, between 1 kDa and 10 kDa, or between 3 kDa and 10 kDa.

The block copolymer can be a PLGA-PC block copolymer having the structure

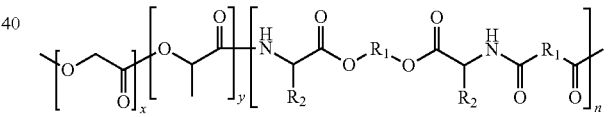

or a PLGA-PC-PEG block copolymer having the structure

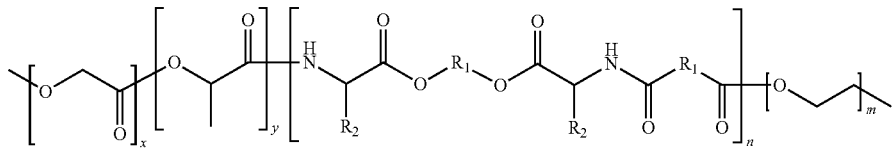

where each $R_1$ is independently a substituted or unsubstituted alkyl, alkenyl, alkynyl, cycloalkyl, heterocycloalkyl, cycloalkenyl, heterocycloalkenyl, aryl, or heteroaryl; each $R_2$ is independently a linear or branched alkyl, alkenyl, cycloalkyl, heterocycloalkyl, cycloalkenyl, heterocycloalkenyl, aryl, or heteroaryl group substituted with one or more cationic primary, secondary, or tertiary amino groups or quaternary ammonium, sulfonium or phosphinium groups; and x, y, n, and m are integers between 1 and 10,000, between 1 and 5,000, between 10 and 1,000, or between 10 and 500. In some embodiments $R_1$ is a substituted or unsubstituted alkyl, alkenyl, alkynyl, cycloalkyl, heterocycloalkyl, cycloalkenyl, heterocycloalkenyl, aryl, or heteroaryl containing from 1 to 30 carbon atoms, from 1 to 20 carbon atoms, from 1 to 12 carbon atoms, or from 2 to 10 carbon atoms. $R_1$ can be a linear or branched alkyl, substituted alkyl, alkenyl, substituted alkenyl, alkylene oxide, or substituted alkylene oxide. Exemplary $R_1$ groups include linear and branched alkyl and substituted alkyl, alkenyl, oralkylene oxide containing from 2 to 20, preferably from 2 to 12 carbon atoms. In preferred embodiments at least one $R_2$ is a cationic hydrophilic side chain containing from 1 to 12 carbon atoms. Each $R_2$ can independently be aliphatic amine, cycloaliphatic amine, heterocyclic amine or aromatic amine, provided that on at least one $R_2$ there is at least one positively charged amine group in the side chain. The positively charged amine group can have a pKa greater than 5.0, greater than 7.0, greater than 9.0, greater than 11.0, greater than 11.5, greater than 12.0, or greater than 12.5. In some embodiments the positively charged amine groups has a pKa between 5.0 and 12.5, between 5.0 and 10.5, between 5.0 and 9.0, or between 6.0 and 8.0. $R_2$ can be the side chain of cationic amino acids such as lysine, arginine and histidine, homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

C. Conjugates

The polymer can include a conjugate of the polymers described above with one or more additional moieties. Conjugates can include the polycations and the polycation containing block copolymers having end-to-end linkages with additional moieties. The additional moiety can be a targeting moiety, a lipid, a protective group, a reactive coupling group, a detectable label, or a therapeutic, prophylactic, or diagnostic agent. For example, the conjugate can have the structure X—PC—Z or X—PC—Y—Z, where X, PC, and Y are as described above and Z is a targeting moiety, a lipid, a protective group, a reactive coupling group, a detectable label, or a therapeutic, prophylactic, or diagnostic agent. Z can be the end group of the polymer, e.g. Z can be a reactive coupling group such as —NH, —COOH, or —SH.

The targeting moiety may refer to elements that bind to or otherwise localize the nanoparticles to a specific locale. The locale may be a tissue, a particular cell type, or a subcellular compartment. The targeting moiety can be an antibody or antigen binding fragment thereof, an aptamer, or a small molecule (less than 500 Daltons). The targeting moiety may have an affinity for a cell-surface receptor or cell-surface antigen on a target cell and result in internalization of the particle within the target cell.

The conjugate can also contain a detectable label, such as, a radioisotope, a fluorophore (e.g., fluorescein isothiocyanate (FITC), phycoerythrin (PE)), an enzyme (e.g., alkaline phosphatase, horseradish peroxidase), element particles (e.g., gold particles) or a contrast agent. In other embodiments the label is a contrast agent. A contrast agent refers to a substance used to enhance the contrast of structures or fluids within the body in medical imaging. Contrast agents are known in the art and include, but are not limited to agents that work based on X-ray attenuation and magnetic resonance signal enhancement. Suitable contrast agents include iodine and barium.

III. Particles

Particles are provided containing one or more of the polycations or one or more of the polycation containing block copolymers described above. The particles can contain one or more anionic therapeutic, prophylactic, or diagnostic agents. The particles can be microparticles or nanoparticles, although nanoparticles are preferred. Representative nanoparticles contain a polycation or a polycation containing block copolymer and an anionic therapeutic, prophylactic, or diagnostic agent.

The nanoparticles may have any desired size for the intended use. The nanoparticles may have any diameter from 10 nm to 1,000 nm. The nanoparticle can have a diameter between 10 nm and 900 nm, between 10 nm and 800 nm, between 10 nm and 700 nm, between 10 nm and 600 nm, between 10 nm and 500 nm, between 20 nm and 500 nm, between 30 nm and 500 nm, between 40 nm and 500 nm, between 50 nm and 500 nm, between 50 nm and 400 nm, between 50 nm and 350 nm, between 50 nm and 300 nm, or between 50 nm and 200 nm. In preferred embodiments the nanoparticles can have a diameter less than 400 nm, less than 300 nm, or more preferably less than 200 nm.

A. Polymers

The particles, including microparticles and nanoparticles, contain one or more polycations or polycation containing copolymers as described above. The polycation or polycation containing copolymer can be present with additional polymers.

The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(ε-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker.

The particles can contain one or more hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly (hydroxy acids); poly(vinyl alcohol), and copolymers thereof.

The particles can contain one or more hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In certain embodiments, the hydrophobic polymer is an aliphatic polyester. In preferred embodiments, the hydrophobic polymer is poly(lactic acid), poly(glycolic acid), or poly(lactic acid-co-glycolic acid).

The particles can contain one or more biodegradable polymers. Biodegradable polymers can include polymers that are insoluble or sparingly soluble in water that are converted chemically or enzymatically in the body into water-soluble materials. Biodegradable polymers can include soluble polymers crosslinked by hydolyzable crosslinking groups to render the crosslinked polymer insoluble or sparingly soluble in water.

Biodegradable polymers in the particle can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene poly(ethylene glycol), poly(ethylene oxide), poly (ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly (ortho esters), poly(ethylene imines), poly(caprolactones), poly(hydroxybutyrates), poly(hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In particularly preferred embodiments the nanoparticle contains biodegradable polyesters or polyanhydrides such as poly(lactic acid), poly(glycolic acid), and poly(lactic-co-glycolic acid).

The particles can contain one or more amphiphilic polymers. Amphiphilic polymers can be polymers containing a hydrophobic polymer block and a hydrophilic polymer block. In some embodiments the amphiphilic polymer is a polycation containing copolymer as described above. The hydrophobic polymer block can contain one or more of the hydrophobic polymers above or a derivative or copolymer thereof. The hydrophilic polymer block can contain one or more of the hydrophilic polymers above, one or more polycations above, or a derivative or copolymer thereof. In some preferred embodiments the amphiphilic polymer is a di-block polymer containing a hydrophobic end formed from a hydrophobic polymer and a hydrophilic end formed of a hydrophilic polymer. In some embodiments, a moiety can be attached to the hydrophobic end, to the hydrophilic end, or both. The amphiphilic polymer can be a tri-block copolymer containing a hydrophobic end formed of a hydrophobic polymer and a hydrophilic end formed of a polycation block and a hydrophilic polymer block. The nanoparticle can contain two or more amphiphilic polymers. For example, the nanoparticle may contain an amphiphilic PLGA-PC block copolymer as described above and a PLGA-PEG block copolymer.

In preferred embodiments the particles contain a first amphiphilic polymer having a hydrophobic polymer block and a hydrophilic polymer block containing a polycation, and a second amphiphilic polymer having a hydrophobic polymer block and a hydrophilic polymer block but without the polycation. The hydrophobic polymer block of the first amphiphilic polymer and the hydrophobic polymer block of the second amphiphilic polymer may be the same or different. In other preferred embodiments the particles contain a first polymer that is an amphiphilic polymer having a hydrophobic polymer block and a hydrophilic polymer block containing a polycation, and a second polymer that is a hydrophobic polymer. The hydrophobic polymer block of the first polymer and the hydrophobic polymer of the second polymer may be the same or different.

B. Anionic Active Agents

The nanoparticles contain one or more exogenous anionic molecules, such as a therapeutic, prophylactic, or diagnostic agent. The nanoparticle can contain one or more proteins, peptides, or analogues thereof, one or more nucleic acids, or a combination thereof. The nanoparticle can contain one or more small molecule anionic active agents, one or more high molecular weight anionic active agents, or a combination thereof.

A protein can be, for example, a protein drug, an antibody, an antibody fragment, a recombinant antibody, a recombinant protein, an enzyme, or the like. Proteins can include DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

Anionic protein analogues can include anionic proteins with modifications such as, for example, acetylation, phosphorylation and myristilation, as well as those containing non-naturally-occurring amino acids, amino acid variants and/or non-peptide inter-amino acid linkages. Modifications can include the addition of a chemical entity such as a carbohydrate group, a phosphate group, a farnesyl group, an isofarnesyl group, a fatty acid group, a linker for conjugation, functionalization, or other modification, etc.

Nucleic acids can include RNA, DNA; synthetic or semi-synthetic derivatives of DNA and RNA, cDNA, or nucleic acid analogs such as phosphorothioates, phosphoramidates, or phosphonates analogs, anti-sense RNA, plasmid DNA. Nucleic acids can be single- or double-stranded; can be linear, branched or circular; and can be of any length. Nucleic acids can include modified bases, sugars and/or mternucleotide linkages. Nucleic acid analogues include polyamide (peptide) nucleic acids and chimeric molecules comprising PNA and/or DNA and/or RNA. Nucleic acids include those capable of forming duplexes and those capable of forming triplex structures with double-stranded DNA.

C. Outer Layer

The particles can contain one or more out layers. The outer layer(s) can stabilize the particles against degradation or provide stealth-properties to avoid immune detection and increase circulation half-life. The outer layer can include one or more of a biodegradable polymer, a stealth polymer, a lipid, a surfactant, or a polymer-lipid conjugate. The protective layer can be present in an amount between 1% and 60%, between 1% and 50%, between 1% and 30%, or between 1% and 20% (w/w) based upon the weight of the particle.

The biodegradable polymer can be any of the biodegradable polymers described above. Preferred biodegradable polymers include hydrophilic polyesters, poly(ortho esters), poly(ethylene imines), poly(caprolactones), poly(hydroxybutyrates), poly(hydroxyvalerates), polyanhydrides, poly(acrylic acids), and polyglycolides.

The stealth polymer can include homo polymers or copolymers of polyalkene glycols, such as poly(ethylene glycol), poly(propylene glycol), poly(butylene glycol), and may include acrylates and acrylamide, such as hydroxyethyl methacrylate and hydroxypropylmethacrylamide respectively.

In preferred embodiments the stealth polymer is poly (ethylene glycol). The lipid can be any synthetic or naturally derived lipid. In preferred embodiments the lipid is an amphiphilic lipid such as phospholipids, phosphoric acid esters, galactolipids, sphingomyelin (sphingolipids), galactose fat, sugar-based ester and/or phosphatidylcholine base. The lipid can be a phospholipid, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used. In some embodiments the lipid is lecithin. Lecithin has an advantage of being a natural lipid that is available from, e.g., soybean, and already has FDA approval for use in other delivery devices. In addition, a mixture of lipids such as lethicin is more advantageous than one single pure lipid. The amphiphilic lipid can have a molecular weight between 200 g/mol and 1,000 g/mol, e.g., 700-900 g/mol.

Suitable surfactants may include anionic, cationic, amphoteric or nonionic surfactants. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

A polymer-lipid conjugate can include end-to-end linkages between a lipid, such as those described above, and a polymer, including a biodegradable polymer and/or a stealth polymer. In preferred embodiments the polymer-lipid conjugate is a PEG-lipid conjugate. PEG-lipid conjugates include, but are not limited to, PEG coupled to dialkyloxypropyls, PEG coupled to diacylglycerols (DAG), PEG coupled to cholesterol, PEG coupled to phosphatidylethanolamines, PEG conjugated to ceramides (see, e.g., U.S. Pat. No. 5,885,613); cationic PEG lipids; cationic-polymer-lipid conjugates (CPLs). Examples of PEG-modified lipids include PEG-modified phosphatidylethanolamine and phosphatidic acid, PEG-ceramide conjugates {e.g., PEG-CerC14 or PEG-CerC20) which are described in copending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols. In one embodiment, the PEG-lipid conjugate is 3-N-[(-methoxypoly(ethylene glycol)2000)carbamoyl]-1,2-dimyristyloxy-propylamine (PEG-DMG). PEG-lipid conjugates are also described, e.g., in U.S. Pat. Nos. 5,820,873, 5,534,499 and 5,885,613.

D. Cationic Particle Core

The nanoparticles in some embodiments contain a cationic particle core. The cationic particle core contains one or more polycations or polycation containing copolymers described above. The cationic polymer core can also contain one or more additional polymers including the hydrophobic, hydrophilic, and biodegradable polymers described above.

The cationic particle core can be used to form the various core-shell nanoparticles (see FIGS. 4A-4D for examples) and multi-core shell nanoparticles (see FIG. 5) described below. In preferred embodiments the cationic polymer core contains a block copolymer having a hydrophobic polymer block and a hydrophilic polycation block, e.g. the PLGA-PC block copolymers described above. The cationic particle core can have a core-shell structure with a hydrophobic inner region containing hydrophobic polymer and a charged outer region containing the polycation or polycation block. The cationic particle core can contain a mixture of 2, 3, 4, or more polymers. In preferred embodiments the cationic polymer core contains a block copolymer having a hydrophobic polymer block and a hydrophilic polycation block and a second polymer containing the hydrophobic polymer without the polycation block. For example, the cationic particle core can contain a PLGA-PC block copolymer and a PLGA homopolymer. See FIGS. 4A-4E. The properties of the cationic particle core, including the particle size and surface zeta potential can be modified by varying the length of the PC or PLGA chain in the copolymer, by changing the ratio of PLGA-PC to PLGA homopolymer, by changing the structure of the polycation polymer, or a combination thereof.

The cationic particle core can have any diameter from about 1 nm to about 300 nm, although in preferred embodiments the cationic particle core has a diameter between 10 nm and 300 nm, between 10 nm and 100 nm, between 20 nm and 80 nm, or between 20 nm and 40 nm. The cationic particle core can have a large surface zeta potential of greater than +10 mV, greater than +20 mV, greater than +30 mV, or greater than +40 mV. The cationic particle cores can have a surface zeta potential value between 0 and +100 mV, between +5 mV and +80 mV, between +10 mV and +60 mV, or between +15 mV and +50 mV.

E. Core-Shell Nanoparticles

Nanoparticles are provided having various core-shell structures. In preferred embodiments the nanoparticles contain a cationic polymer core as described above in combination with the anionic active agent, optionally including protective layers described above. The strong electrostatic interactions between the cationic particle core and the anionic active agent provide strong physical adsorption of the anionic active agents around the cationic particle core. The particle thus forms a core-shell structure with the cationic particle core surrounded by a thick layer of the anionic active agents. The anionic active agents can form a layer around the cationic particle core having a thickness up to about 1 micron, 800 nm, 600 nm, 500 nm, 250 nm, 100 nm, 75 nm, 50 nm, 40 nm, 30 nm, or up to about 20 nm.

Figures 4A, 4B:
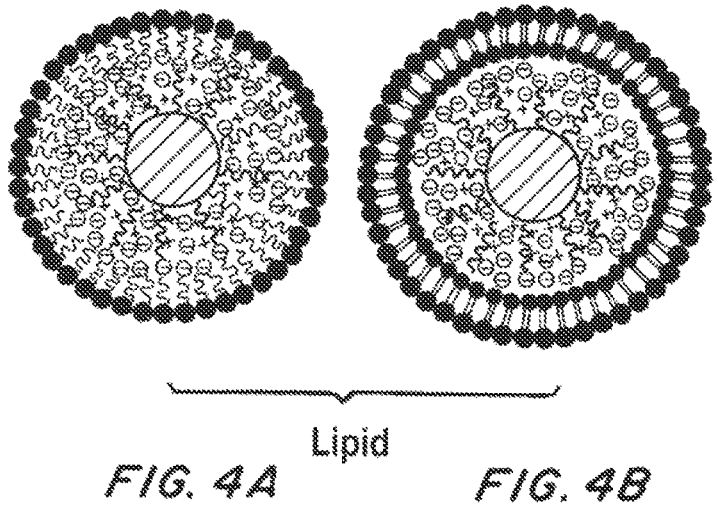
FIGS. 4A-4E depict some of the particle structures that can be produced using the polycation containing polymers.

The core-shell nanoparticles can contain a lipid monolayer (e.g. FIG. 4A) or lipid bilayer (e. g. FIG. 4B) shell. Exemplary embodiments provide a core-shell nanoparticle having (1) a cationic particle core; (2) an outer lipid layer; and (3) a layer of anionic active agent dispersed between the cationic particle core and the lipid layer. Additional moieties such as targeting moieties can be attached to the exterior surface of the lipid.

Figures 4C, 4D, 4E:
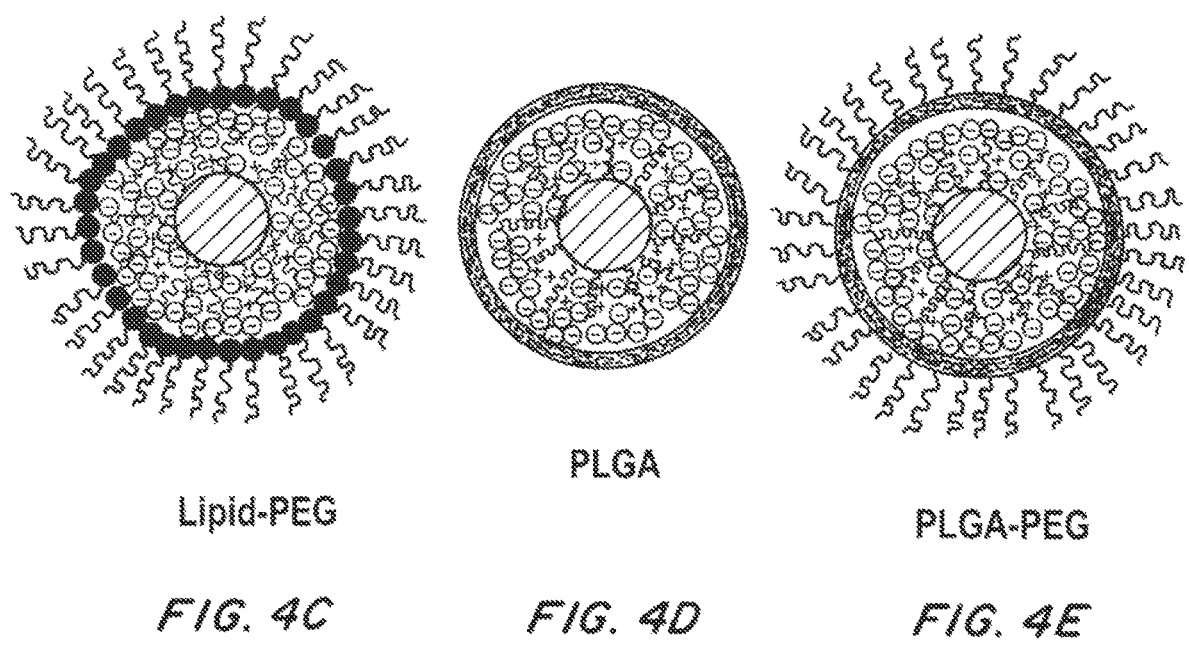

The core-shell nanoparticles can contain a polymer-lipid conjugate (e.g. FIG. 4C). Exemplary embodiments provide a core-shell nanoparticle having (1) a cationic particle core; (2) a layer containing a polymer-lipid conjugate; and (3) a layer of anionic active agent dispersed between the cationic particle core and the polymer-lipid conjugate layer. Additional moieties such as targeting moieties can be attached to the exterior surface, e.g. attached covalently or non-covalently to the polymer-lipid conjugate. For example a core-shell particle is provided containing (1) a cationic particle core containing a blend of PLGA and a block-copolymer having the structure PLGA-PC where PC is a polycation polymer described above; (2) a layer of a Z-PEG-lipid conjugate where Z is a targeting moiety targeting a specific tissue, cell type or subcellular; and (3) a layer of anionic active agent dispersed between the cationic particle core and the Z-PEG-lipid conjugate layer.

Core-shell nanoparticles can contain an outer polymer layer that can be a biodegradable polymer layer, a stealth polymer layer, or both (e.g. FIG. 4D and FIG. 4E). For example, a core-shell particle can have (1) a cationic particle core; (2) a layer containing a biodegradable polymer; and (3) a layer of anionic active agent dispersed between the cationic particle core and the biodegradable polymer layer. The biodegradable polymer layer can contain one or a mixture of 2, 3, 4, or more polymers. The biodegradable polymer layer can contain any biodegradable and biocompatible polymer. The biodegradable polymer layer can contain a hydrophobic polymer, a hydrophilic polymer, or copolymers thereof. In preferred embodiments the core-shell particle contains (1) a cationic particle core; (2) a layer containing an amphiphilic copolymer having a hydrophobic polymer block and a hydrophilic polymer block; and (3) a layer of anionic active agent dispersed between the cationic particle core and the amphiphilic polymer layer.

D. Multi-Core-Shell Nanoparticles

Figure 5:
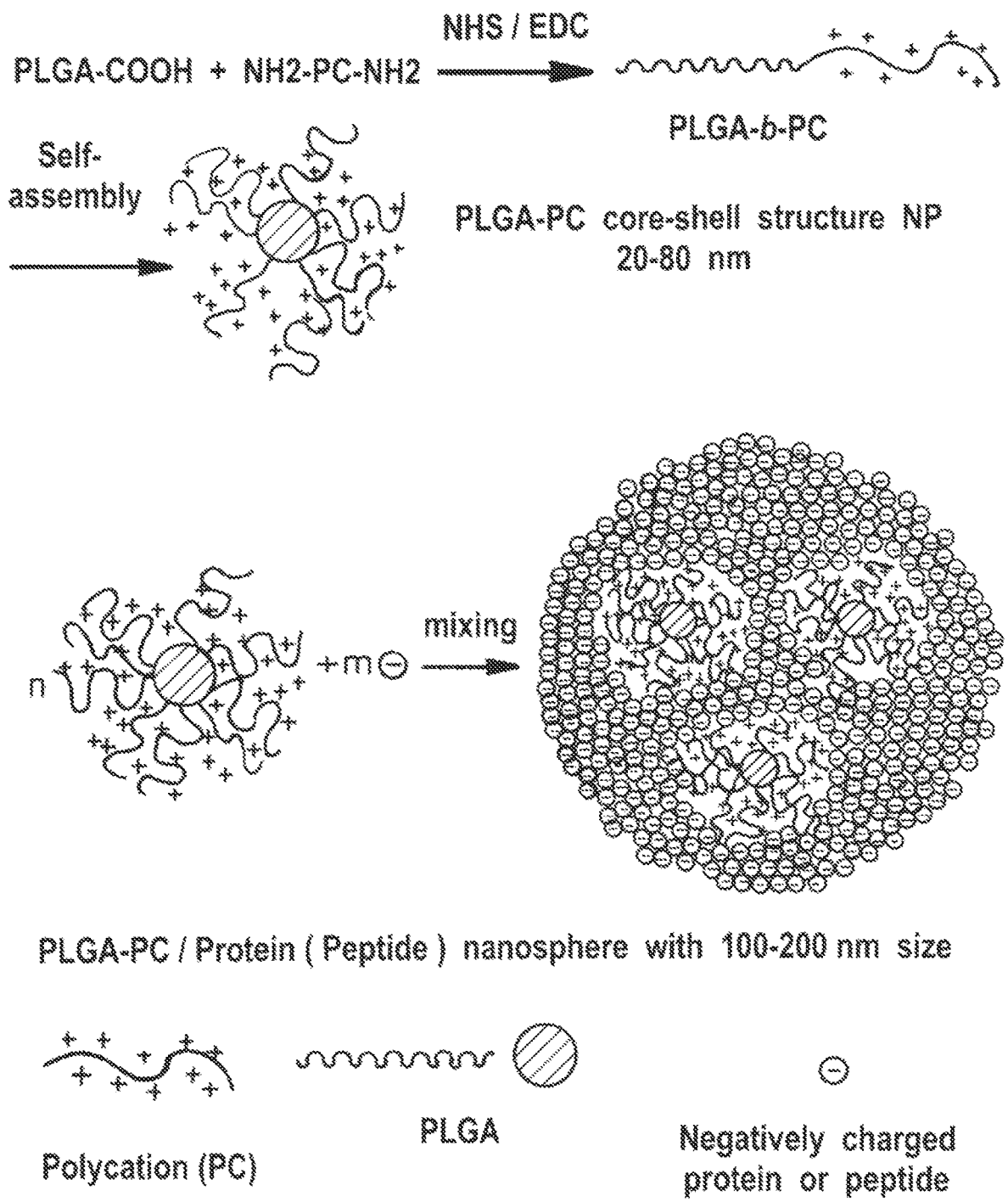
FIG. 5 is a schematic depicting formation of small nanoparticles having a cationic outer later from self-assembly of block copolymers of a hydropobic biodegradable polymer (PLGA) and a polycation (PC). The small nanoparticles self-assemble with anionic active agents such as proteins, nucleic acids, or peptides to form a multinuclear PLGA-PC/ protein nanosphere.

Multi-core shell nanoparticles are also provided. The multi-core shell nanoparticles contain 2, 3, 4, or more cationic nanoparticle cores in combination with the anionic active agent, optionally containing a protective layer. In one embodiment a multi-core shell nanoparticle is provided having 3 cationic particle cores dispersed throughout and encompassed within the anionic active agents, optionally containing additional excipients or stabilizers, for example, as depicted in FIG. 5. The multi-core shell nanoparticle may have any diameter up to about 1 micron, although smaller particles are preferred. In some embodiments the multi-core shell nanoparticles have a diameter between 20 nm and 1,000 nm, between 20 nm and 800 nm, between 50 nm and 500 nm, between 50 nm and 400 nm, between 50 nm and 300 nm, between 100 nm and 220 nm, or between 100 nm and 200 nm.

The multi-core shell nanoparticles may contain any number of cationic particle cores, e.g. between 2 and 100, between 2 and 50, between 2 and 10, or between 2 and 5. The multi-core shell nanoparticle can contain 2, 3, 4, or more cationic particle cores.

Multi-core shell nanoparticles are provided containing (1) a plurality of cationic particle cores and (2) a layer of anionic active agents encapsulating the cationic particle cores. The cationic particle cores are distributed within the interior of the multi-core shell nanoparticle. The multi-core shell nanoparticle can contain a protective layer surrounding the anionic active agents, e.g. lipid monolayers or bilayers, polymer-lipid conjugate layers, and/or biodegradable polymer layers.

Exemplary embodiments provide a core-shell nanoparticle having (1) a plurality of cationic particle cores encapsulated by and dispersed within a plurality of anionic active agents to form a particle and (2) a protective outer layer. The protective outer layer can be a lipid monolayer, a lipid bilayer, a polymer-lipid conjugate layer, or a biodegradable polymer layer. Additional moieties such as targeting moieties can be attached to the exterior surface, e.g. attached covalently or non-covalently to the lipid, polymer, or polymer-lipid conjugate.

An exemplary embodiment provides a multi-core-shell nanoparticle containing a plurality of cationic particle cores encapsulated by and dispersed within a plurality of anionic active agents to form a particle, where the cationic particle cores contain a blend of PLGA and a block-copolymer having the structure PLGA-PC where PC is a polycation polymer described above.

IV. Formulations

The formulations described herein contain an effective amount of the particles in a pharmaceutical carrier appropriate for administration to an individual in need thereof. In some embodiments the formulations contain nanoparticles. The formulations can be administered parenterally (e.g., by injection or infusion), enterally, topically (e.g., to the eye), or via pulmonary administration.

A. Parenteral Formulations

The nanoparticles can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the nanopaarticles can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s) or nanoparticles.

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the nanoparticles in the required amount in the appropriate solvent or dispersion medium with one or more of the excipients listed above, as required, followed by filtered sterilization. Generally, dispersions are prepared by incorporating the various sterilized nanoparticles into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the nanoparticle plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for parenteral administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for parenteral administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as PURITE®), phenylmercuric acetate, chlorobutanol, sorbic acid, chlorhexidine, benzyl alcohol, parabens, thimerosal, and mixtures thereof. Solutions, suspensions, or emulsions for parenteral administration may also contain one or more excipients known art, such as dispersing agents, wetting agents, and suspending agents.

B. Topical Formulations

The nanoparticles can be formulated for topical administration. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the nanoparticles can be administered as a liquid formulation, such as a solution or suspension, a semi-solid formulation, such as a lotion or ointment, or a solid formulation. In some embodiments, the nanoparticles are formulated as liquids, including solutions and suspensions, such as eye drops or as a semi-solid formulation, such as ointment or lotion for topical application to the skin, to the mucosa, such as the eye or vaginally or rectally.

The formulation may contain one or more excipients, such as emollients, surfactants, emulsifiers, and penetration enhancers.

C. Enteral Formulations

The nanoparticles can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

D. Pulmonary Formulations

The nanoparticle can be prepared for pulmonary administration. The nanoparticles may be alone or in combination with additional active agents, pharmaceutically acceptable carriers, pharmaceutically acceptable excipients, or combinations thereof. The pharmaceutical carrier and excipient are composed of materials that are considered safe and effective and may be administered to an individual without causing undesirable biological side effects or unwanted interactions.

Formulations for pulmonary administration can be administered using methods known in the art. Suitable methods can include, but are not limited to, dry powder inhalers, pressurized metered-dose inhalers, nebulizers and aerosolizers, electrodynamic aerosol generators, and endotracheal aerosol generators.

In the case of pulmonary administration, formulations can be divided into dry powder formulations and liquid formulations. Both dry powder and liquid formulations can be used to form aerosol formulations. Useful formulations, and methods of manufacture, are described by Caryalho, et al., J Aerosol Med Pulm Drug Deliv. 2011 April; 24(2):61-80. Epub 2011 Mar. 16, for delivery of chemotherapeutic drugs to the lungs.

Dry Powder Formulations

Dry powder formulations are finely divided solid formulations containing one or more nanoparticles which are suitable for pulmonary administration. Dry powder formulations include one or more nanoparticles. Such dry powder formulations can be administered via pulmonary inhalation to a patient without the benefit of any carrier, other than air or a suitable propellant. Preferably, however, the dry powder formulations contain one or more nanoparticles in combination with a pharmaceutically acceptable carrier.

The pharmaceutical carrier may include a bulking agent, such as carbohydrates (including monosaccharides, polysaccharides, and cyclodextrins), polypeptides, amino acids, and combinations thereof. Suitable bulking agents include fructose, galactose, glucose, lactitol, lactose, maltitol, maltose, mannitol, melezitose, myoinositol, 50ryptococc, raffinose, stachyose, sucrose, trehalose, xylitol, hydrates thereof, and combinations thereof.

The pharmaceutical carrier may include a lipid or surfactant. Natural surfactants such as dipalmitoylphosphatidylcholine (DPPC) are the most preferred. This is commercially available for treatment of respiratory distress syndrome in premature infants. Synthetic and animal derived pulmonary surfactants include: Synthetic Pulmonary Surfactants such as EXOSURF® (a mixture of DPPC with hexadecanol and tyloxapol added as spreading agents); PUMACTANT® (Artificial Lung Expanding Compound or ALEC®); a mixture of DPPC and PG; KL-4 (composed of DPPC, palmitoyl-oleoyl phosphatidylglycerol, and palmitic acid, combined with a 21 amino acid synthetic peptide that mimics the structural characteristics of SP-B); and VENTICUTE® (DPPC, PG, palmitic acid and recombinant SP-C) or animal derived surfactants such as ALVEOFACT® (extracted from cow lung lavage fluid); CUROSURF® (extracted from material derived from minced pig lung; INFASURF® (extracted from calf lung lavage fluid); and SURVANTA® (extracted from minced cow lung with additional DPPC, palmitic acid and tripalmitin). EXOSURF®, CUROSURF®, INFASURF®, and SURVANTA® are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending the one or more nanoparticles with a pharmaceutical carrier. Optionally, additional active agents may be incorporated into the mixture as discussed above. The mixture is then formed into particles suitable for pulmonary administration using techniques known in the art, such as lyophilization, spray drying, agglomeration, spray coating, extrusion processes, hot melt particle formation, phase separation particle formation (spontaneous emulsion particle formation, solvent evaporation particle formation, and solvent removal particle formation), coacervation, low temperature casting, grinding, milling (e.g., air-attrition milling (jet milling), ball milling), high pressure homogenization, and/or supercritical fluid crystallization.

An appropriate method of particle formation can be selected based on the desired particle size, particle size distribution, and particle morphology. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

Liquid Formulations

Liquid formulations contain one or more nanoparticles, possibly with one or more additional active agents, dissolved or suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propylp-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as an alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In the context of pulmonary formulations, "minor amounts" means no excipients are present that might adversely affect uptake of the one or more active agents in the lungs.

Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment. Preferably, a dry powder or liquid formulation as described above is formulated into aerosol formulations using one or more propellants.

V. Methods of Making Polymers

Methods of polymer synthesis are described, for instance, in Braun et al. (2005) Polymer Synthesis: Theory and Practice. New York, N.Y.: Springer. The polymers may be synthesized via step-growth polymerization, chain-growth polymerization, or plasma polymerization.

A. Methods of Making Polycations

Methods of making polycations containing the structural formula described above are well known in the art and as described herein. For example, in some embodiments a polycation containing an α-amino acid can be obtained by converting the α-amino acid into a bis-(α-amino acid) diester monomer, for example, by condensing the α-amino acid with a diol. As a result, ester bonds are formed. Then, the bis-(α-amino acid) diester is reacted by a polycondensation reaction with a di-acid, such as sebacic acid, to obtain the final co-polymer having both ester and amide bonds.

Alternatively, instead of the di-acid, an activated di-acid derivative, e.g., a bis-(p-nitrophenyl) diester, can be used as an activated di-acid.

B. Methods of Making Copolymers

In some embodiments an block copolymer or amphiphilic block copolymer is synthesized starting from a hydrophobic polymer terminated with a first reactive coupling group and a hydrophilic polymer terminated with a second reactive coupling group capable of reacting with the first reactive coupling group to form a covalent bond. The hydrophilic polymer, hydrophobic polymer, or both can be a polycation or a polycation containing polymer. One of either the first reactive coupling group or the second reactive coupling group can be a primary amine, where the other reactive coupling group can be an amine-reactive linking group such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. One of either the first reactive coupling group or the second reactive coupling group can be an aldehyde, where the other reactive coupling group can be an aldehyde reactive linking group such as hydrazides, alkoxyamines, and primary amines. One of either the first reactive coupling group or the second reactive coupling group can be a thiol, where the other reactive coupling group can be a sulfhydryl reactive group such as maleimides, haloacetyls, and pyridyl disulfides.

In preferred embodiments a hydrophobic polymer terminated with an amine or an amine-reactive linking group is coupled to a hydrophilic polymer or a polycation polymer terminated with complimentary reactive linking group. For example, an NHS ester activated PLGA can be formed by reacting PLGA-CO(OH) with NHS and a coupling reagent such as dicyclohexylcarbodiimide (DCC) or ethyl(dimethylaminopropyl) carbodiimide (EDC). The NHS ester activated PLGA can be reacted with a hydrophilic polymer or a polycation polymer terminated with a primary amine, such as a PEG-NH$_2$ or PC—NH$_2$ to form an amphiphilic PLGA-b-PEG or a PLGA-b-PC block copolymer respectively.

In some embodiments a conjugate of an amphiphilic polymer with a targeting moiety is formed using the same or similar coupling reactions. In some embodiments the conjugate is made starting from a hydrophilic polymer terminated on one end with a first reactive coupling group and terminated on a second end with a protective group. The hydrophilic polymer is reacted with a targeting moiety having a reactive group that is complimentary to the first reactive group to form a covalent bond between the hydrophilic polymer and the targeting moiety. The protective group can then be removed to provide a second reactive coupling group, for example to allow coupling of a hydrophobic polymer block to the conjugate of the hydrophilic polymer with the targeting moiety. A hydrophobic polymer terminated with a reactive coupling group complimentary to the second reactive coupling group can then be covalently coupled to form the conjugate. Of course, the steps could also be performed in reverse order, i.e. a conjugate of a hydrophobic polymer and a hydrophilic polymer could be formed first followed by deprotection and coupling of the targeting moiety to the hydrophilic polymer block.

In some embodiments a conjugate is formed having a moiety conjugated to both ends of the amphiphilic polymer. For example, an amphiphilic polymer having a hydrophobic polymer block and a hydrophilic polymer block may have targeting moiety conjugated to the hydrophilic polymer block and an additional moiety conjugated to the hydrophobic polymer block. In some embodiments the additional moiety can be a detectable label. In some embodiments the additional moiety is a therapeutic, prophylactic, or diagnostic agent. For example, the additional moiety could be a moiety used for radiotherapy. The conjugate can be prepared starting from a hydrophobic polymer having on one end a first reactive coupling group and a another end first protective group and a hydrophilic polymer having on one end a second reactive coupling group and on another end a second protective group. The hydrophobic polymer can be reacted with the additional moiety having a reactive coupling group complimentary to the first reactive coupling group, thereby forming a conjugate of the hydrophobic polymer to the additional moiety. The hydrophilic polymer can be reacted with a targeting moiety having a reactive coupling group complimentary to the second reactive coupling group, thereby forming a conjugate of the hydrophilic polymer to the targeting moiety. The first protective group and the second protective group can be removed to yield a pair of complimentary reactive coupling groups that can be reacted to covalently link the hydrophobic polymer block to the hydrophilic polymer block.

VI. Methods of Making Polycation Containing Nanoparticles

A. Emulsion Methods

In some embodiments, a nanoparticle is prepared using an emulsion solvent evaporation method. For example, a polymeric material is dissolved in a water immiscible organic solvent and mixed with a drug solution or a combination of drug solutions. In some embodiments a solution of a therapeutic, prophylactic, or diagnostic agent to be encapsulated is mixed with the polymer solution. The polymer can be, but is not limited to, one or more of the following: PLA, PGA, PCL, their copolymers, polyacrylates, the aforementioned PEGylated polymers, the aforementioned Polymer-drug conjugates, the aforementioned polymer-peptide conjugates, or the aforementioned fluorescently labeled polymers, or various forms of their combinations. The drug molecules can be, but are not limited to, one or a more of the following: PPARgamma activators (e.g. Rosiglitazone, (RS)-5-[4-(2-[methyl(pyridin-2-yl)amino]ethoxy)benzyl]thiazolidine-2, 4-dione, Pioglitazone, (RS)-5-(4-[2-(5-ethylpyridin-2-yl) ethoxy]benzyl)thiazolidine-2,4-dione, Troglitazone, (RS)-5-(4-[(6-hydroxy-2,5,7,8-tetramethylchroman-2-yl)methoxy] benzyl)thiazolidine-2,4-dione etc.), prostagladin E2 analog (PGE2, (5Z,11α,13E,15S)-7-[3-hydroxy-2-(3-hydroxyoct-1-enyl)-5-oxo-cyclopentyl] hept-5-enoic acid etc.), beta3 adrenoceptor agonist (CL 316243, Disodium 5-[(2R)-2-[[(2R)-2-(3-Chlorophenyl)-2-hydroxyethyl]amino]propyl]-1,3-benzodioxole-2,2-dicarboxylate hydrate, etc.), Fibroblast Growth Factor 21 (FGF-21), Irisin, RNA, DNA, chemotherapeutic compounds, nuclear magnetic resonance (NMR) contrast agents, or combinations thereof. The water immiscible organic solvent, can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and Dimethyl sulfoxide (DMSO).

In some embodiments the polymer solution contains one or more polycations or polycation containing polymers as described above. The polymer solution can contain a first amphiphilic polymer conjugate having a hydrophobic polymer block and a hydrophilic polymer block that is or contains a polycation described above. In preferred embodiments the polymer solution contains one or more additional polymers or amphiphilic polymer conjugates. For example the polymer solution may contain, in addition to the first amphiphilic polymer conjugate, one or more hydrophobic polymers, hydrophilic polymers, lipids, amphiphilic polymers, polymer-drug conjugates, or conjugates containing other targeting moieties. By controlling the ratio of the first amphiphilic polymer to the additional polymers or amphiphilic polymer conjugates, the density of the polycation can be controlled. The first amphiphilic polymer may be present from 1% to 100% by weight of the polymers in the polymer solution. For example, the first amphiphilic polymer can be present at 10%, 20%, 30%, 40%, 50%, or 60% by weight of the polymers in the polymer solution.

An aqueous solution is then added into the resulting mixture solution to yield emulsion solution by emulsification. The emulsification technique can be, but not limited to, probe sonication or homogenization through a homogenizer.

B. Nanoprecipitation Method

In another embodiment, a polycation containing nanoparticle is prepared using nanoprecipitation methods or microfluidic devices. The polycation containing polymeric material, optionally mixed with a drug or drug combinations in a water miscible organic solvent, and optionally containing additional polymers. The additional polymer can be, but is not limited to, one or more of the following: PLA, PGA, PCL, their copolymers, polyacrylates, the aforementioned PEGylated polymers. The water miscible organic solvent, can be, but is not limited to, one or more of the following: acetone, ethanol, methanol, isopropyl alcohol, acetonitrile and Dimethyl sulfoxide (DMSO). The resulting mixture solution is then added to a polymer non-solvent, such as an aqueous solution, to yield nanoparticle solution. The plaque-targeted peptides or fluorophores or drugs may be associated with the surface of, encapsulated within, surrounded by, and/or distributed throughout the polymeric matrix of this inventive particle.

C. Microfluidics

Methods of making nanoparticles using microfluidics are known in the art. Suitable methods include those described in U.S. Patent Application Publication No. 2010/0022680 A1 by Karnik et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

VII. Methods of Using Polycation Containing Nanoparticles and Formulations Thereof The formulations described herein can be used for the delivery of a therapeutic, prophylactic, or diagnostic agent to an individual or patient in need thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate enteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic The present invention will be further understood by reference to the following non-limiting examples.

EXAMPLES

Materials and Methods

L-arginine, p-toluenesulfoninc acid monohydrate, succinyl chloride, adipoyl chloride, sebacoyl chloride, 1,2-ethanediol, 1,3-propanediol, 1,4-butanediol, triethylamine, p-nitrophenol, 3-(4,5-Dimethylthiazol-2-yl)-2,5-diphenyltetrazolium bromide (MTT), N-Hydroxysuccinimide (NHS), and 1-Ethyl-3-(3-dimethylaminopropyl)carbodiimide (EDC) were all purchased from Sigma-Aldrich (St. Louis, Mo.) and used without further purification. Organic solvents such as amethanol, toluene, ethyl acetate, ethyl ether, 2-propanol, and dimethyl sulfoxide (DMSO) were purchased from VWR Scientific (West Chester, Pa.) and were purified by standard methods before use.

Two types of PLGAs with one carboxylic acid end group (PLGA-COOH) were purchased from Lactel absorbable polymers and used without further purification. High molecular weight PLGA1 (50/50, viscosity: 0.55-0.75 dL/g) and low molecular weight PLGA2 (50/50, viscosity: 0.15-0.25 dL/g) have $M_n$ around 45 kDa and 5.0 kDa, respectively, when measured by GPC with THF solvent. AC2-26 peptide (AMVSEFLKQAWFIENEEQEYVQTVK) was purchased from Tocris Biosciences. BSA, insulin, ovalbumin, and α-lactalbumin were all purchased from Sigma-Aldrich (St. Louis, Mo.) and used directly.

Hela, PC3, and A549 cell lines were obtained from American Type Culture Collection (ATCC, Manassas, Va.). All the cells were grown per the recommended ATCC protocols. The cell lines were used from passages 5 to 12. Growth media was changed every 2 days. Cells were grown to 70% confluence before splitting, harvesting, or transfection. Dulbecco's modified eagle medium (DMEM), penicillin-streptomycin (PS, 100 U/mL), trypsin-EDTA (TE, 0.5% trypsin, 5.3 mM EDTA tetra-sodium), fetal bovine serum (FBS) were obtained from Gibco BRL (Rockville, Md.). Other cell culture related chemicals, reagents, and buffers were purchased from Sigma-Aldrich (St. Louis, Mo.) unless otherwise specified.

Materials, nanoparticles, and complexes were characterized by various standard methods. For Fourier transform infrared (FTIR) characterization, the samples were ground into a powder and mixed with KBr at a sample/KBr ration of 1:10 (w/w). FTIR spectra were obtained with a PerkinElmer (Madison, Wis.) Nicolet Magana 560 FTIR spectrometer with Omnic software for data acquisition and analysis. 1H-NMR spectra were recorded on a Brukner AVANCED-400 NMR spectrometer. Deuterated water (D2O-d2; Cambridge Isotope Laboratories, Andover, Mass.) with tetramethylsilane as an internal standard or denatured dimethyl sulfoxide (DMSO-d6; Cambridge Isotope Laboratories, Andover, Mass.) were used as the solvent. MestReNova software was used for data analysis. The molecular weight of the polymers was measured by GPC, using THF or 0.1% (w/v) LiCl in DMAc solution as solvents. The polymers were prepared at a concentration of 1 mg/mL (w/v) in solvent. The sample molecular weights were determined from a standard curve generated from polystyrene standards that were chromatographed under the same conditions as the samples. The solubility of the polymers in common organic solvents at room temperature was assessed using 1.0 mg/mL as a solubility criterion. The quantitative solubility of polymers in distilled water at room temperature was measured by adding distilled water drop by drop until a clear solution was obtained. The NP sizes and ζ-potentials were obtained using quasi-electric laser light scattering using a ZetaPALS dynamic light scattering detector (15 mW laser, incident beam ¼ 676 nm; Brookhaven Instruments). Electron microscopy (EM) was performed at the Harvard Medical School EM facility on a Tecnai G2 Spirit BioTWIN EM.

Where appropriate, the data are presented as mean±standard deviation calculated over at least three data points. JMP software (version 8.0, from SAS Company) was used for data analysis. Significant differences compared to control groups were evaluated by unpaired Student's t-test or Dunnet test at p 0.05, and between more than two groups by Tukey's test with or without one-way ANOVA analysis of variance.

Example 1. Synthesis of L-Arginine Polycation Polymers

A water-soluble L-arginine-based polycation (PC) library was developed according to a modified synthesis protocol of (Wu et al., Adv. Func. Mat., 2012, 22: 3815; Wu et al., J. Mat. Chem., 22: 18983 (2012). The PCs were prepared via polycondensation between two monomers: di-p-nitorphenyl esters of dicarboxylic acid monomers (monomers I) and tetra-p-toluenesulfonic acid salts of bis (L-arginine), a, co-alkylene diesters (monomers II).

Di-p-nitrophenyl esters of dicarboxylic acids (monomers I) were prepared by reacting dicarboxylic acyl chloride varying in methylene length with p-nitrophenyl (Wu et al., J. Mat. Chem., 22: 18983 (2012)). Three monomers were prepared: di-p-nitrophenyl succinate (NSu with x=2); di-p-nitrophenyl adipate (NA with x=4); and di-p-nitrophenyl sebacate (NS with x=8), wherein the 'x' indicates the number of methylene groups in the diacid. For example, di-p-nitrophenyl adipate (NA) was prepared by the reaction of adipoyl chloride (0.15 mol) with p-nitrophenol (0.31 mol) in acetone in the presence of triethylamine (0.32 mol). The p-nitrophenol and triethylamine acetone solution (400 mL) was maintained at 0° C. using an ice/water bath. Adipoyl chloride was diluted in 100 mL of cold acetone and added dropwise to the p-nitrophenol and triethylamine acetone solution with stirring for 2 h at 0° C. and overnight at room temperature. The resulting di-p-nitrophenyl adipate was precipitated in distilled water, washed completely, and then dried in vacuo at room temperature before final recrystallization in ethyl acetate. The purification process was performed three times. The final product was recovered as a brown colored crystal.

Tetra-p-toluenesulfonic acid salts of bis (L-arginine), α, ω-alkylene diesters (monomers II) were prepared according to Yamanouchi, et al., Biomaterials 29:3269 (2008). The following is an example of a synthesis protocol for tetra-p-toluenesulfonic acid salt of bis (L-arginine) butane diesters. L-arginine (0.04 mol) and 1, 4-butanediol (0.02 mol) were directly mixed in a three neck round bottom flask with toluene (400 mL, b.p. 110° C.) with the presence of p-toluenesulfonic acid monohydrate (0.082 mol). The solid-liquid reaction mixture was heated to 130° C. and reflux with stirring for 24 hr with 2.16 mL (0.12 mol) of water generate.

The reaction mixture (viscous solid) was then cooled to room temperature. Toluene was decanted. The resulting product was finally purified by dissolving the product in 2-propanol at 75° C. with stirring and then precipitating at 4° C. for three times. The ideal precipitation time is around 12 h. 2-propanol was changed each time after precipitating and decanted afterwards, and the white sticky mass was dried in vacuo. The final product was a white powder. Three monomers II were made: tetra-p-toluenesulfonic acid salt of bis (L-arginine) ethane diesters, Arg-2-S, (y=2); tetra-p-toluenesulfonic acid salt of bis (L-arginine) propane diesters, Arg-3-S (y=3); tetra-p-toluenesulfonic acid salt of bis (L-arginine) butane diesters, Arg-4-S (y=4); S indicates that the Arg diester monomer is in the p-toluenesulfonic acid salt form. The monomers are a white solid powder. The chemical structures of all the monomers I and II were confirmed by $^1$HNMR.

The arginine based polycations (PCs) were prepared by solution polycondensation of the monomers I (NSu, NA and NS) and monomers II (Arg-2-S, Arg-3-S, and Arg-4-S) with a variety of combinations using a modified protocol. The molar ratio of monomers I to II was changed from 1.0/1.0 to designed weight ratios so that PCs could be obtained with controllable end groups and molecular weight. Molar ratios of monomers I to II was varied to be smaller than 1.0 so that the $NH_2$ end groups could be obtained. The specific monomer combinations and weight ratios and the resulting PCs are summarized in Table 1.

An example of the synthesis of the polycation from NS and Arg-2-S with a molar ratio of 9.0 to 10.0 via solution polycondensation is given here. Monomers NS (0.9 mmol) and Arg-2-S (1.0 mmol) in 2.0 mL of dry DMSO were mixed well by vortexing. The mixture solution was heated up to 70° C. with stirring to dissolve the monomers and obtain a uniformed mixture solution. Triethylamine (0.31 mL, 2.2 mmol) was added drop by drop to the mixture at 70° C. with vigorous stirring until the complete dissolution of the monomers. The solution color turned yellow after several minutes. The reaction vial was then kept for 48 hrs at 70° C. in a thermostat oven without stirring. The resulting solution was precipitated in cold ethyl acetate, decanted, dried, re-dissolved in methanol and re-precipitate in cold ethyl acetate for further purification. The purification was repeated 2 times before drying in vacuo at room temperature. The final PCs are a yellow or pale yellow solid powder. The chemical structures of all the PCs were confirmed by $^1$H NMR. The molecular weights of PCs with molar ratio (I/II) equal to 9/10 were roughly around 9.0-10.0 kDa, while molecular weights of PCs with molar ratio (I/II) equal to 3/5 were roughly around 3.5-4.0 kDa.

The prepared PCs are strongly polar. All prepared PCs are soluble in buffers, distilled water (>1.0 mg/mL) and polar organic solvents like DMSO, DMF and methanol. They are insoluble in non-polar or weak polar organic solvents like ethyl acetate, DCM, chloroform, THF and organic solvents. For the aqueous solubility of PCs developed in this study, the effect of x and y material parameters on PCs water solubility revealed that both x and y had a major impact on the water solubility of PCs. An increase of x or y significantly reduced the water solubility due to the increasing hydrophobicity. For example, PC3 (x=2 and y=3) has a solubility around 10 times of PC 15 (x=8 and y=3) (about 200 mg/mL versus 20 mg/mL).

TABLE 1

Summary of the PC library

| PC Name | X | Y | Molar ratio (I/II) |
| --- | --- | --- | --- |
| PC1 | 2 | 2 | 9/10 |
| PC2 | 2 | 2 | 3/5 |
| PC3 | 2 | 3 | 9/10 |
| PC4 | 2 | 3 | 3/5 |
| PC5 | 2 | 4 | 9/10 |
| PC6 | 2 | 4 | 3/5 |
| PC7 | 4 | 2 | 9/10 |
| PC8 | 4 | 2 | 3/5 |
| PC9 | 4 | 3 | 9/10 |
| PC10 | 4 | 3 | 3/5 |
| pen | 4 | 4 | 9/10 |
| PC12 | 4 | 4 | 3/5 |
| PC13 | 8 | 2 | 9/10 |
| PC 14 | 8 | 2 | 3/5 |
| PC15 | 8 | 3 | 9/10 |
| PC16 | 8 | 3 | 3/5 |
| PC17 | 8 | 4 | 9/10 |
| PC18 | 8 | 4 | 3/5 |

Example 2: Synthesis of Polycation Containing Block Copolymers

Figure 6:
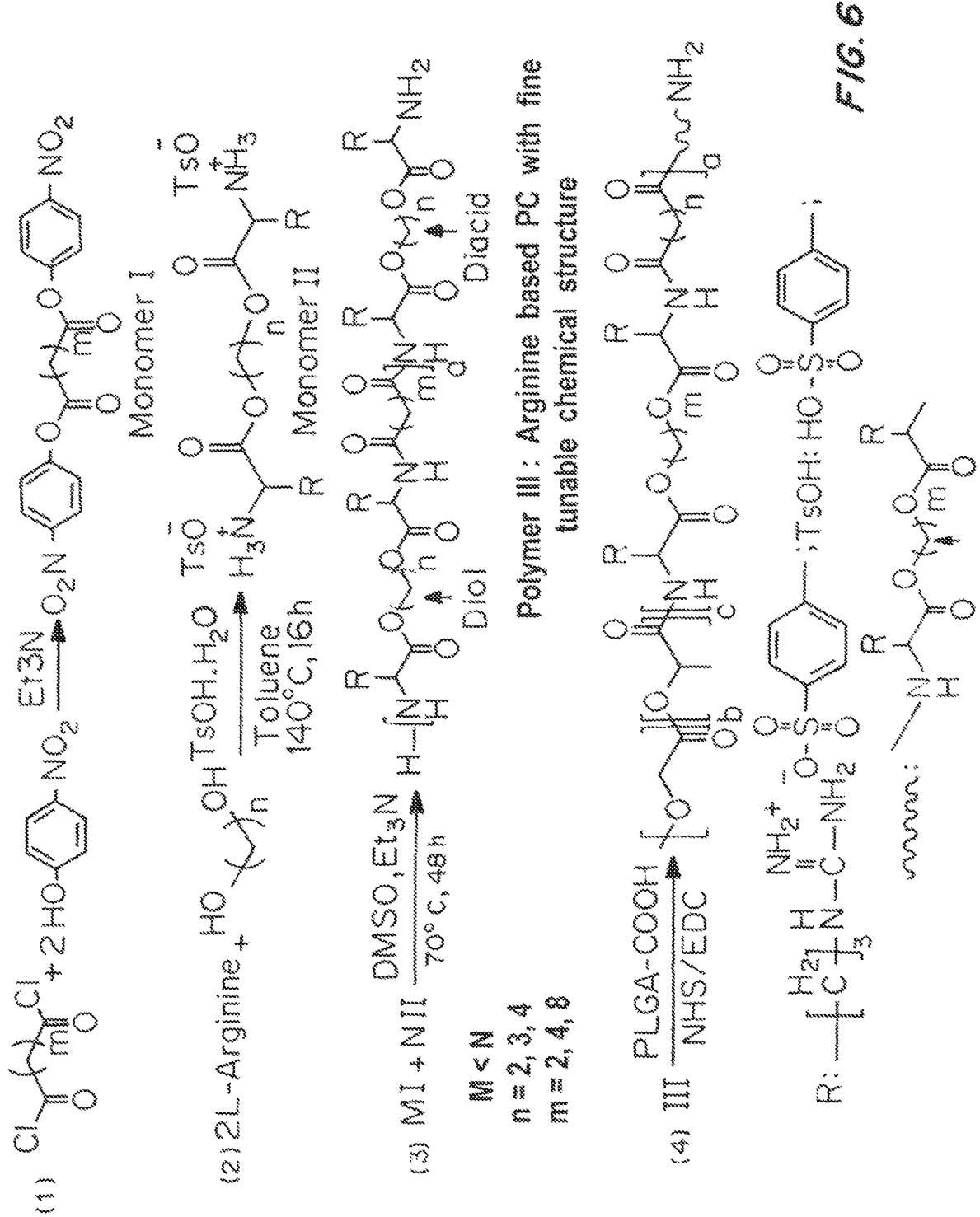
FIG. 6 is a scheme depicting the synthesis of some L-arginine-based polycations (PC) (steps 1-3) and PLGA-b-PC copolymers (step 4).
Figure 7:
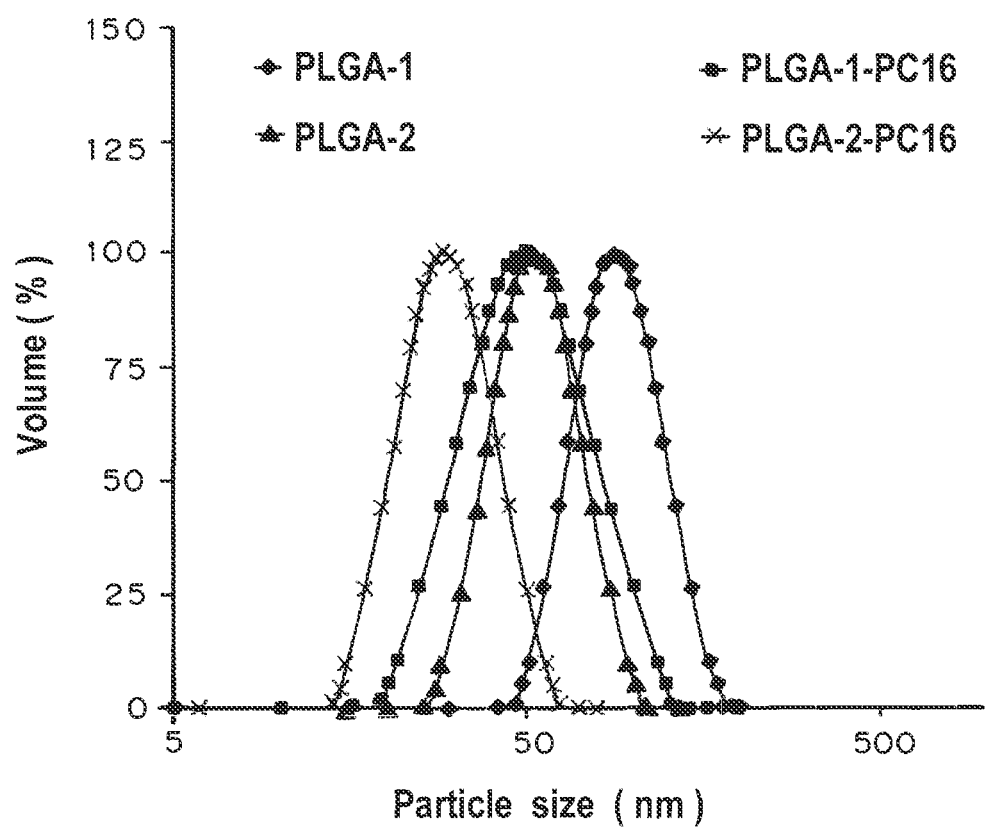
FIG. 7 is a graph depicting the particle size (nm). distribution of the poly(lactide-co-glycolide) (PLGA) and PLGA-block-polycation (PLGA-b-PC) nanoparticles measured by dynamic light scattering.

Di-block copolymers of PLGA-b-PC were prepared by coupling the carboxy terminal of PLGA and the amino functionality of PC via 1-ethyl-3-(3-dimethylaminopropyl) carbodiimide hydrochloride (EDC) and N-hydroxysuccinimide (NHS) activation methodology (FIG. 6).

The obtained PLGA-b-PC copolymers were pale-yellow or yellow solids with high yields (70-90%), depending on the PLGA-b-PC composition. The prepared di-block copolymers of PLGA-b-PC were named PLGAy-PCx. Two types of PLGA-COOH with significantly different MWs were used: PLGA1 (Mn=43.5 kDa) and PLGA2 (Mn=5.0 kDa). The chemical structures of prepared PLGA-b-PC copolymers were confirmed by $^1$NMR. This example indicates that the percentage of PLGA-PC cationic moiety could be altered by changing the PLGA MW, an important factor for NP functionality.

PLGA-PC polycations were prepared by conjugating NH2-PC—NH2 to PLGA-COOH via the NHS/EDC chemistry route. The reaction conditions for the synthesis PLGA-PC polycations were exemplified by the following example protocol:

1. Dissolve 500 mg of PLGA-carboxylate (high molecular weight, around 0.01 mmol) in 2.0 mL dichloromethane (DCM).
2. Dissolve NHS (6.0 mg, 0.05 mmol) and EDC (9.6 mg, 0.05 mmol) in 1.0 mL DCM.
3. PLGA-carboxylate is converted into PLGA-NHS by adding the EDC/NHS solution to a PLGA carboxylate solution with gentle stirring for 3 hours.
4. PLGA-NHS is precipitated with 40 mL cold ethyl ether/methanol washing solvent by centrifugation at 2,700×g for 10 min to remove residual EDC/NHS.
5. Repeat washing and centrifugation two times.
6. The PLGA-NHS pellet is dried under vacuum for 12 hours to remove residual ether and methanol.
7. After drying under vacuum, PLGA-NHS (200 mg, 0.004 mmol) is dissolved in DMSO (5.0 mL) followed by addition of PC3 with $NH_2$ end groups (120 mg, around 0.012 mmol) and DIEA (15.0 mg, 0.012 mmol). The mixture solution is incubated for 24 h at room temperature under gentle stirring.

8. Precipitate the resulting PLGA-6-PC block copolymer with ether/methanol washing solvent and centrifuge to remove unreacted PC and other impurities.
9. Repeat washing and centrifugation two times.
10. Dry the purified PLGA-fr-PC polymer under vacuum. The final products of PLGA-i-PCs are white or white-yellow powder or viscous solid. The prepared PLGA-PCs are insoluble in buffers and distilled water and the organic solvents like methanol, ethyl acetate, ACN, ethyl ether, but soluble in polar organic solvents like DMSO and DMF. Some of them have low solubility (a few mg/mL) in DCM, chloroform and THF, depending on the copolymer composition. They should be stored at −20° C. for long term storage. The polymer structure is confirmed by $^1$HNMR.

Example 3: Characterization of PLGA-b-PC Nanoparticles

Materials and Methods

PLGA-b-PC copolymers could be fabricated into variable nanostructures through different methods, including nanoprecipitation, single emulsion, and double emulsion. The nanoprecipitation method was chosen, because the resulting PLGA-PC NPs would have the desired core (PLGA)-shell (PC) structure with small size while still being simple, fast to manufacture, and reproducible.

Because of the insolubility of PLGA-PCs in many organic solvents, DMSO was used as the organic solvent for the nanoprecipitation step. First, PLGA-6-PC (20 mg/mL) was dissolved in DMSO. Then the polymer solution was added dropwise to 19 volumes of stirring distilled water with or without surfactants giving a final polymer concentration of 1.0 mg/mL. The particle size and size distribution are measured by dynamic light scattering at 25° C., with a scattering angle of 90°, and using a NP concentration of approximately 0.1 to 0.5 mg/mL. The NP surface zeta potential is measured and recorded as the average of three measurements. Transition electron microscopy (TEM) was used to confirm the size and structure of the NPs. A solution of NPs in distilled water (0.1-0.5 mg/mL) was absorbed on grids and negatively stained for 15 seconds. For each sample, 5-6 grids are prepared and viewed. Images were normally taken at 13¬49,000* magnification.

The PLGA-PC NPs were characterized in terms of particle size, surface charge (zeta potential), and particle structure (surface morphology and shape) by a variety of methods. The particle size and surface charge of PLGA-PC NPs are very important for the next step of the formulation and will be discussed in detail below.

Results

The TEM images and DLS results show that the particle size of the PLGA-PC NP formed via nanoprecipitation were mainly in the range of 20-80 nm, depending on the PLGA-PC composition. PLGA MW was the dominating factor for resulting NP size: low-MW PLGA2-based PLGA-PC NPs were mainly in the size range of 20-40 nm; while the high-MW PLGA1-based PLGA-PC NPs were mainly in the size range of 40-80 nm. Compared to the corresponding PLGA NPs, the PLGA-PC NPs were smaller. TEM images demonstrated that the PLGA-PC NPs were spherical or egg shaped, while the surface morphology was fluffy due to the thick PC shell under dry state. The surface charges (zeta potential) of nanoprecipitated NPs were in the range of +15 to 50 my. For these systems, the surface charge of NPs was not correlated with PLGA or PC structure or MW.

The cytotoxicity of PLGA-PC NPs was evaluated via an MTT assay. The PLGA-PC NPs were not toxic to either Hela or PC3 cells in the concentration range of 1.0 ng/mL to 200 µg/mL.

Stability tests of PLGA-PC NPs showed that all nanoprecipitated NPs were stable in PBS buffer or distilled water for weeks with the presence of PVA, TWEEN®-80, lipid, or lipid-polyethylene glycol (PEG).

Example 4: Manufacture of PLGA-PC/BSA Nanoparticles

Although many strategies have been developed for loading NPs with proteins, serious challenges remain regarding easily and safely loading a high quantity of proteins into NPs of reasonably small size. The PLGA-PC NPs were designed with these goals in mind, and it is believed that body charge density, not the surface charge, determines the protein loading efficiency of a NP. In order to better utilize the electrostatic field of the thick PC shell to strongly adsorb proteins and form new NP complexes with desired size and protein loading, a few formulation strategies were tried until a very simple method with the lowest contamination was chosen: direct mixing of aqueous solutions containing PLGA-PC NPs and proteins. Before the systematic study, a quick experiment was carried out to verify this proof of concept by simply mixing random amounts of PLGA-PC NP solutions with BSA solutions.

After mixing there are some changes in terms of zeta potential, particle size, and structure, depending on PLGA-PC type, weight ratio (WR) of PLGA-PC to protein, and other formulation conditions. PLGA1-PC16 NP was mixed with 2 wt % bovine serum albumin (BSA) in aqueous solution. After mixing, each PLGA-PC NP was loaded with some protein. Some NPs aggregated through bound proteins, but the structure of this complex was random and irregular.

For the preparation of PLGA-PC/protein complex, freshly prepared BSA solution (1-5 mg/mL) was quickly added to predetermined volumes of freshly prepared PLGA-PC NP distilled water solution (0.1¬0.5 mg/mL) at a stirring speed of 800-1200 rpm for 60 seconds.

For the preparation of PLGA-PC/protein/Lipid-PEG complex sphere or PLGA-PC/protein/lipid complex sphere, the Lipid-PEG or lipid aqueous solutions freshly prepared then the solutions were quickly mixed with freshly prepared PLGA-PC/protein complex sphere. Then concentrated PBS buffer was added to obtain a final IX concentration of PBS.

Example 5: Characterization of PLGA-PC/BSA Nanoparticles

Materials and Methods

To investigate the relationships among protein loading efficiency, particle size, structure, and surface charge of the PLGA-PC NP/BSA complex, two types of PLGA-PC NPs were selected to systematically investigate the NP-protein interaction and the structure-function relationship. The two types of PLGA-PC NPs (PLGA1-PC16 and PLGA2-PC16) had very similar polymer structure: the PC blocks were identical, while PLGA blocks had the same structure but significantly different MWs (43.5 kDa and 5.0 kDa, respectively). Since the MW of PC16 is around 4.5 kDa, the PC composition of PLGA1-PC16 NP is about 9.4 wt %, while the PC composition of PLGA2-PC16 NP is about 47.4 wt %. Therefore, the two systems have completely different PC composition percentage (a five-fold difference), making comparison straightforward. BSA was used as a model protein due to its suitable size (MW=66.5 kDa) and charge properties (isoelectric point=4.7).

For each PLGA-PC NP system, various PLGA-PC/BSA hybrid complexes were formed by simply mixing aqueous solutions with a series of desired weight ratios ("WRs") of PLGA to BSA, ranging broadly from 5,000 to 2.

Results

Figure 8:
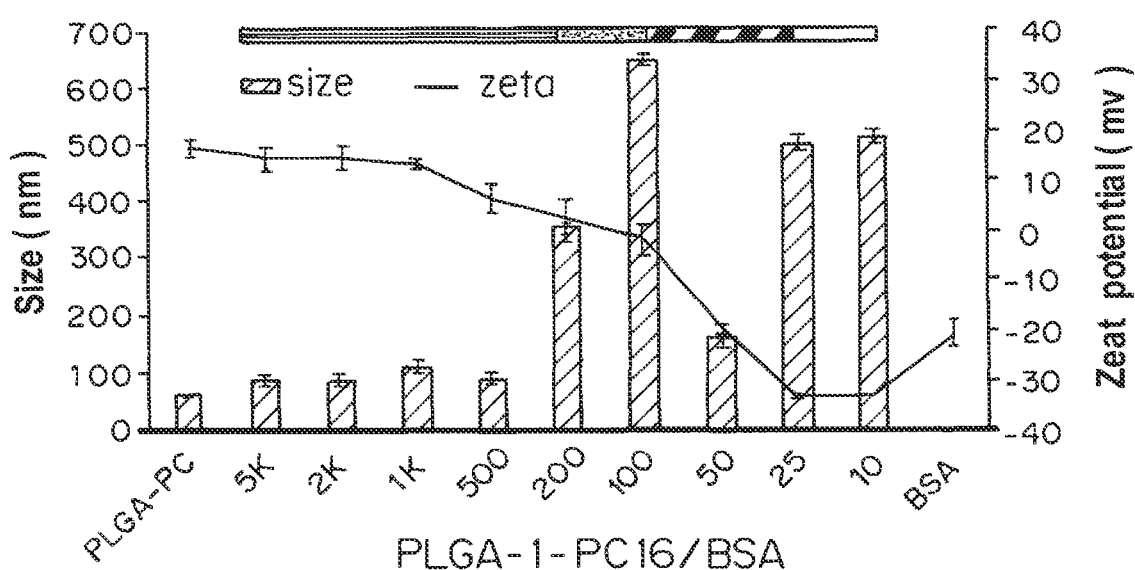
FIG. 8 is a graph depicting the dependence of the particle size (nm; bars) and the zeta potential (mV; line) on the ratio (w/w) of PLGA-PC polymer to bovine serum albumin (BSA) protein for PLGA-1-PC-16/BSA particles.
Figure 9:
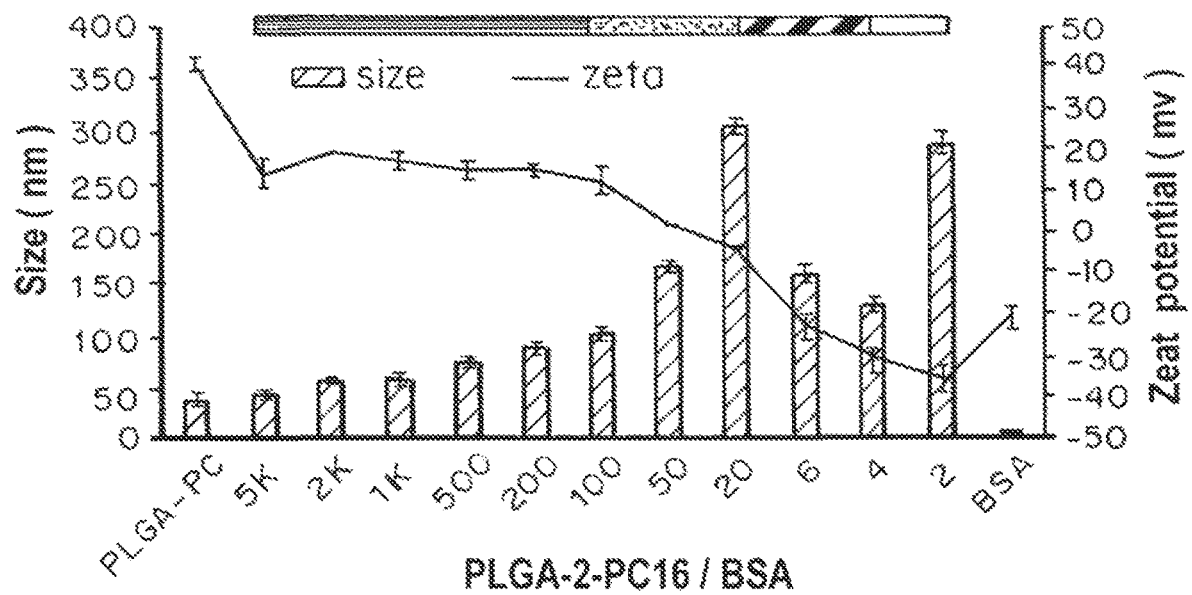
FIG. 9 is a graph depicting the dependence of the particle size (nm; bars) and the zeta potential (mV; line) on the ratio (w/w) of PLGA-PC polymer to bovine serum albumin (BSA) protein for PLGA-2-PC-16/BSA particles.

FIGS. 8 and 9 show the particle size and zeta potential of newly formed PLGA-PC/BSA hybrid particles as a function of the WR of PLGA-PC NP to BSA. The zeta potential trend of FIGS. 8 and 9 can be divided into four regions, depending on the PLGA-b-PC copolymer structure and WR of PLGA-PC NP to protein. In the first region, as the WR of PLGA-PC NP to protein decreased from 5,000 to a few hundred, the zeta potential of the complex particles decreased, indicating that if more proteins were mixed with PLGA-PC NPs, more of the positively charged surface of the PLGA-PC NP was surrounded or covered by negatively charged proteins via electrostatic interaction. In the second region, with more proteins added (WR from a few hundred to a few tens), almost all of the PLGA-PC NP surface was finally covered with proteins and the zeta potential changed from positive to zero or slightly negative. At this stage, the corresponding WR to the 0 my zeta potential is determined by the PLGA-b-PC copolymer composition (PC percentage). For the third region, a further decrease of the WR of PLGA-PC NP to protein continued to decrease the zeta potential of the complexed particle to around −30 my. For the fourth (last) region, the zeta potential continued to decrease or plateaued at a value slightly more negative than the zeta potential of pure BSA.

The particle size trend in FIGS. 8 and 9 can also be divided into the exact same four regions. In the first region, as the WR of PLGA-PC to BSA decreased, the size of the complex particle slightly and steadily increased, suggesting that as more protein was added into the PLGA-PC NP solutions, the PLGA-PC NPs began to interact with or adsorb more proteins on their surface. In the second region, as the WR of PLGA-PC NP to protein decreased further, the particle size of PLGA-PC NP/protein complexes significantly increased beyond the expected size range, indicating some form of aggregation. For the largest particle size obtained in this region, the corresponding zeta potential was around zero, which is reasonable since NPs with neutral surface charge tend to be very unstable. After the second region, however, a continuing decrease of WR in a narrow range (third region) immediately resulted in a significant reduction of complex particle size. This phenomenon suggests that the particle may be in a stable state within this narrow WR range and is likely the optimal formulation. The small particle size had a corresponding zeta potential of approximately −20 my, which confirmed its relatively stable state. In this region, the PLGA2-PC system had loaded protein in the range of 15-30 wt % with encapsulation efficiency over 95%. However, for the PLGA1-PC system, the corresponding protein loading was in the range of 2-3 wt % due to the low PC density. In the fourth (last) region, the continuously decreasing WR caused significant particle size increases, indicating aggregation. Thus, at very high BSA concentrations, stable complexes were unable to form, and a large portion of BSA remained free.

These results show that for each type of PLGA-PC NP, the maximum effective loading efficiency was achieved at a small particle size with a zeta potential range of −10 to −30 mv, in a narrow WR range of PLGA-PC to BSA. FIGS. 8 and 9 show the same trend for both size and zeta potential, but have different corresponding WR windows for the specific small particle size, suggesting that this is a function of polymer structure. These relationships also exist for other PLGA-PC NPs.

In the third region of the PLGA2-PC system the complexed particles had small sizes but maintained significant protein loading. TEM was used to study the complexed particle structure in this region for the PLGA2-PC system. To acquire better image quality and resolve more details, the formulation protocol was slightly modified so that larger NPs could be obtained without affecting structure. PLGA2-PC/BSA NPs with relatively large size at a WR of 4 were obtained after simple mixing. The structure and surface morphology of the complexed NPs were different from the pure PLGA-PC NPs. Based on the NP size and protein loading, it was predicted that multiple PLGA-PC NPs were contained in a single, complexed NP. Through TEM, the inner structure of complexes was examined, confirming that there were multiple PLGA-PC NPs inside, acting as the nucleus for each complexed NP.

For the specific PLGA2-PC/Protein nanospheres formed in the third region, the unmodified, complexed nanospheres were found to be unstable in buffered solutions. To improve stability, a variety of strategies were tested. It was found that lipid and lipid-PEG both effectively stabilized these nanospheres in buffer. For example, 1,2-distearoylsn-glycero-3-phosphoethanolamine-N-methoxy (polyethylene glycol) (DSPE-PEGm) stabilized the PLGA2-PC/Protein nanospheres in buffer, additionally increasing the size by around 50 nm (while still keeping it below 200 nm) with only a 10 wt % decrease in overall protein loading.

Example 6: BSA Loading and Release from PLGA-PC/BSA Nanoparticles

Materials and Methods

The release profile of the PLGA2-PC/protein nanosphere coated with DSPE-PEGm nanospheres in PBS buffer was studied.

BCA assay was used to measure the loaded and released protein in this report. All the steps are exactly following the manufacturer's protocol. A serial dilution of pure protein solutions with predetermined concentrations were used to make standard curve every time. For the measurement of protein loading and release, since the PC component of PLGA-PC NPs has a lot of amino acids and will affect the BCA results, the supernatant solution was collected and the inside free unloaded proteins were analyzed via BCA assay.

Results

Figure 10:
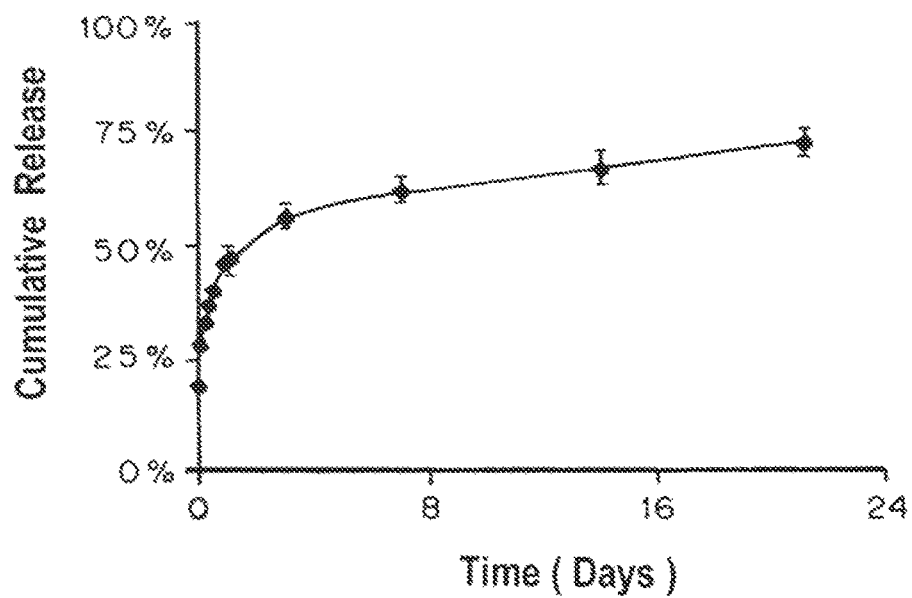
FIG. 10 is a graph depicting the release profile of PLGA-PC NP/BSA/Lipid PEG in PBS buffer.

As shown in FIG. 10, some burst release (around 20 wt %) was observed after the addition of buffers, with fast release occurring over the first 1-2 days, especially in the initial hours. After a few hours, release of BSA was sustained and steady for at least three weeks.

Figure 11:
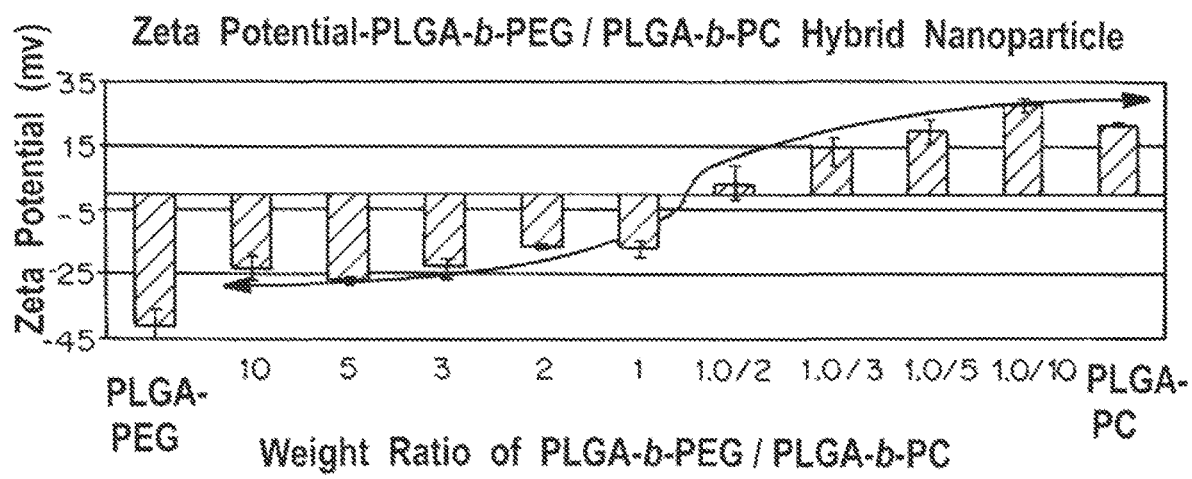
FIG. 11 is a bar graph depicting the dependence of the zeta potential (mV) on the ratio (w/w) of PLGA-b-PEG to PLGA-b-PC. The PEG is 3.4K.

FIG. 11 is a bar graph depicting the dependence of the zeta potential (mV) on the ratio (w/w) of PLGA-b-PEG to PLGA-b-PC. The PEG is 3.4K.

Figure 12:
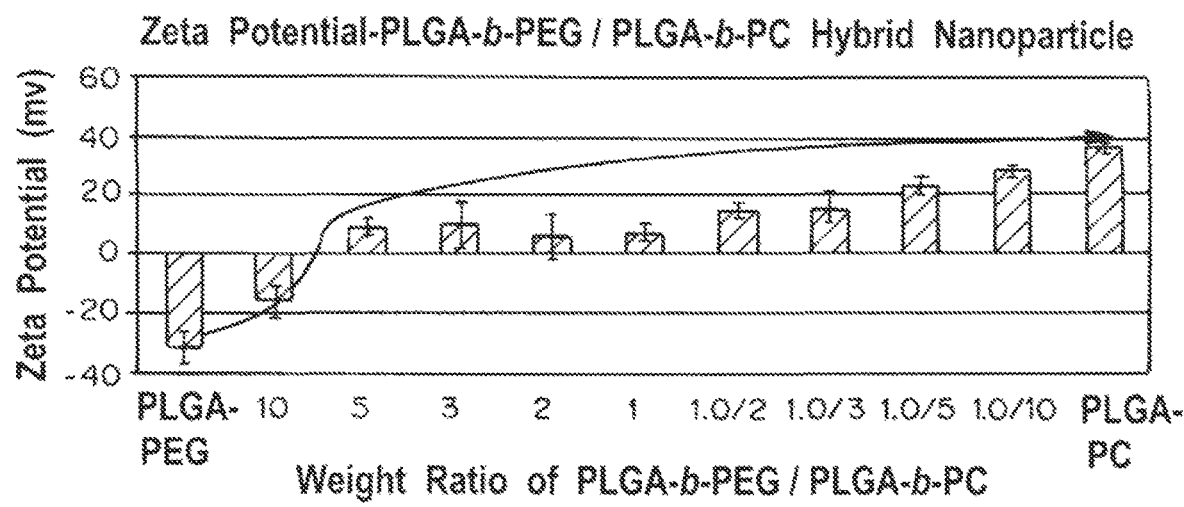
FIG. 12 is a bar graph depicting the dependence of the zeta potential (mV) on the ratio (w/w) of PLGA-b-PEG to PLGA-b-PC. The PEG is 2K.

FIG. 12 is a bar graph depicting the dependence of the zeta potential (mV) on the ratio (w/w) of PLGA-b-PEG to PLGA-b-PC. The PEG is 2K.

Figure 13:
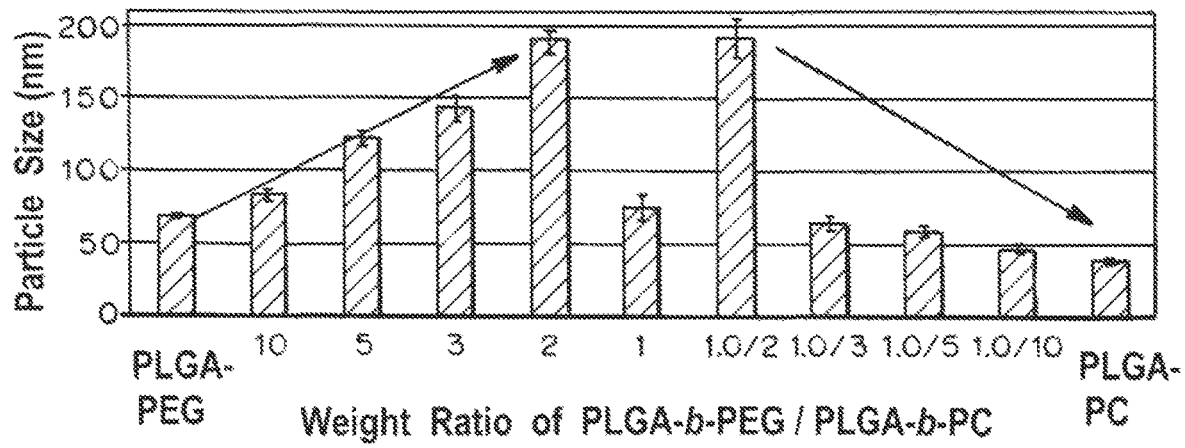
FIG. 13 is a bar graph depicting the dependence of the particle size (nm) from dynamic light scattering on the ratio (w/w) of PLGA-b-PEG to PLGA-b-PC. The PEG is 3.4K.

FIG. 13 is a bar graph depicting the dependence of the particle size (nm) from dynamic light scattering on the ratio (w/w) of PLGA-b-PEG to PLGA-b-PC. The PEG is 3.4K.

Figure 14:
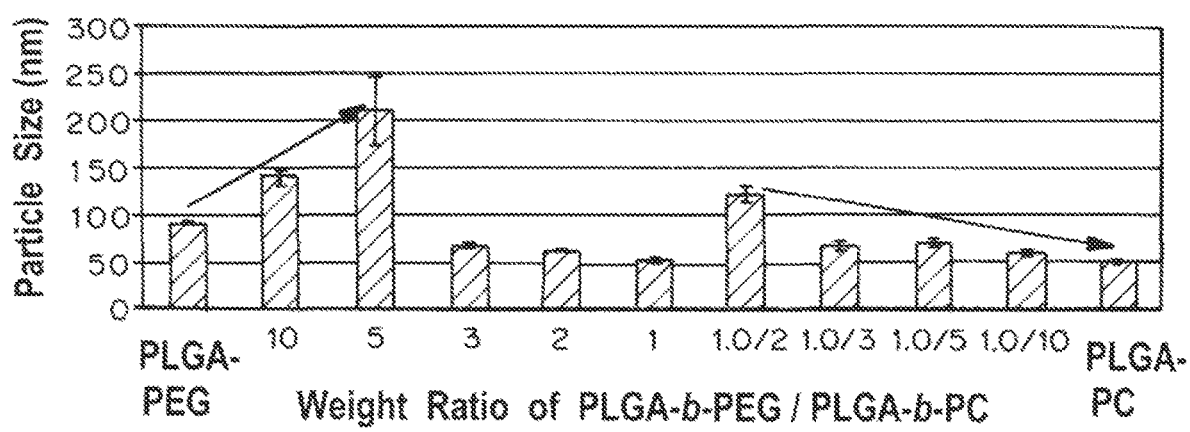
FIG. 14 is a bar graph depicting the dependence of the particle size (nm) from dynamic light scattering on the ratio (w/w) of PLGA-b-PEG to PLGA-b-PC. The PEG is 2K.

FIG. 14 is a bar graph depicting the dependence of the particle size (nm) from dynamic light scattering on the ratio (w/w) of PLGA-b-PEG to PLGA-b-PC. The PEG is 2K.

Example 7: PLGA-PC Loading of Other Proteins/Peptides

Materials and Methods

Besides BSA, the interaction between PLGA-PC NPs and other negatively charged proteins/peptides was also evaluated using ovalbumin, α-lactalbumin, insulin, and Ac2-26 peptide as models, with MWs around 45.0, 14.0, 6.0, and 3.0 kDa, respectively.

Results

Figure 15:
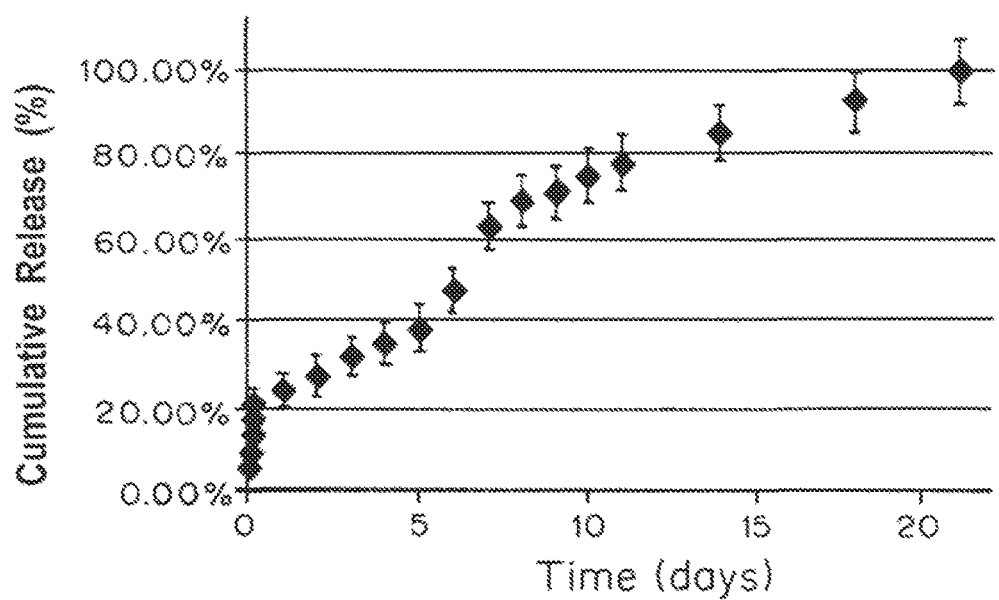
FIG. 15 is a graph of the cumulative insulin release (%) as a function of time (days) for PLGA-PC/insulin nanoparticles prepared by nanoprecipitation.

FIG. 15 is a graph of the cumulative insulin release (%) as a function of time (days) for PLGA-PC/insulin nanoparticles prepared by nanoprecipitation.

Figure 16:
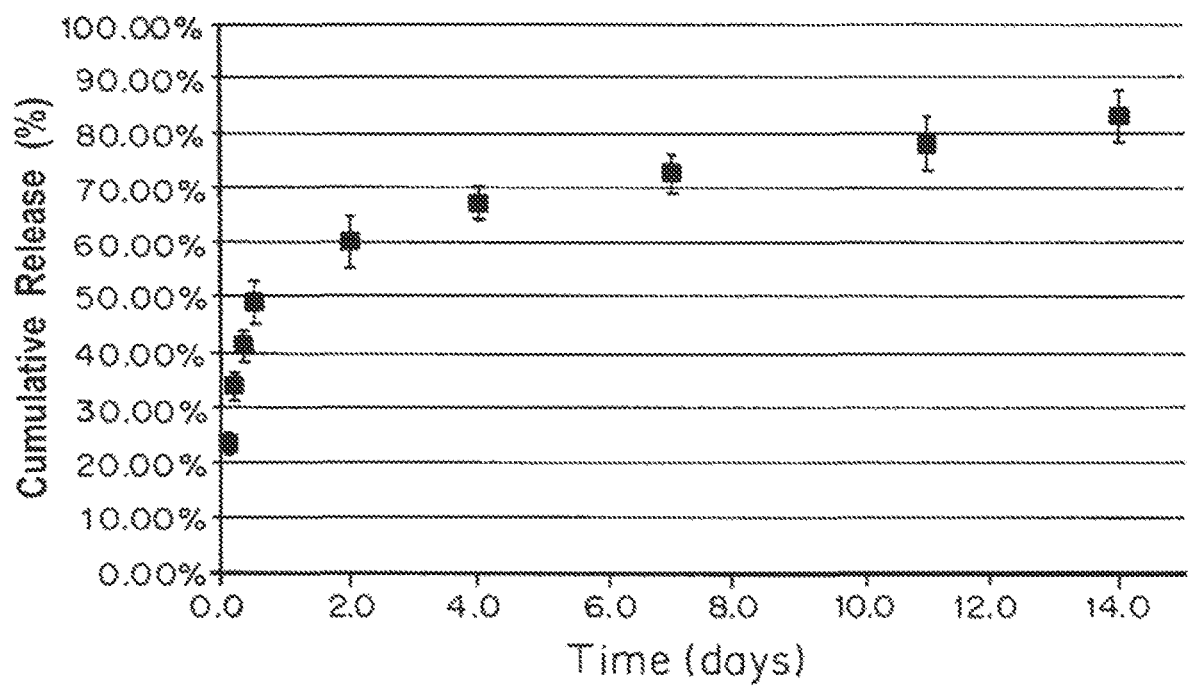
FIG. 16 is a graph of the cumulative insulin release (%) as a function of time (days) for PLGA-PC/insulin nanoparticles prepared by double emulsion.

FIG. 16 is a graph of the cumulative insulin release (%) as a function of time (days) for PLGA-PC/insulin nanoparticles prepared by double emulsion.

Release appears to be faster in the nanopaorticles made by double emulsion than by nanoprecipitation.

Results and relationships were similar to those found above. It was confirmed that the MWs of proteins/peptides did not significantly affect interactions between PLGA-PC NPs and proteins. Additionally, multiple types of negatively charged proteins could be loaded simultaneously without making obvious sacrifices in loading efficiency.

Example 8: Cytotoxicity of PLGA-PC and PLGA-PC/Protein/Lipid-PEG

Materials and Methods

The cytotoxicity of PLGA-PC and PLGA-PC/Protein/Lipid-PEG nanoparticles was evaluated by the MTT assay. An increase in cell number (cell proliferation) results in an increase in the amount of MTT formazan production and hence an increase in UV absorbance at the 570 nm wavelength. Two types of cells, Hela and PC3, were used for the MTT assay. The cultured cells were seeded at an appropriate cell density concentration (3,000 cells/well) in 96-well plates and incubated overnight in a 5% $CO_2$ incubator at 37° C. The cells were then treated with various NP solutions for 4 h. PLGA-PC NP solutions were stabilized with 1.0 wt % polyvinylalcohol ("PVA") or TWEEN®-80. The mixture of media and NPs was removed and complete DMEM was then added into each well for 44 h incubation (total time, 48 h). The cells treated with normal cell culture media only were used as the negative control (NC). After 48 h incubation (total treatment time) of the treated cells at 37° C. and 5% $CO_2$, 15 μL of MTT solution (5 mg/mL) was added to each well, followed by 4 h incubation at 37° C., 5% $CO_2$. Then the cell culture medium was carefully removed and 150 μL of acidic isopropyl alcohol (with 0.1 M HCl) was added to dissolve the formed formazan crystal. OD was measured at 570 nm (subtract background reading at 690 nm) using a VersaMax Tunable Microplate reader. The cell viability was expressed as the percentage of the blank negative control. Triplicates were used in each experiment.

Results

The MTT data clearly demonstrated that, after 4 h treatment, all the nanoparticle samples showed the same as or close to the blank control, i.e., very little cytotoxicity to the cells tested even at a large dosage such as 1 mg/mL.

Example 9: Cellular Uptake of PLGA-PC/BSA/Lipid-PEG Particles

Materials and Methods

BSA proteins were labelled with fluorescent dye Rhodamine-B-Isothiocyanate (RITC) and purified according to manufaufacuter's protocol. The NPs of PLGA-PC/fluorescence BSA/Lipid-PEG (20 wt % BSA) were fabricated following the above protocol. A549 cells were used for this cellular uptake evaluation. The cultured cells were seeded at an appropriate cell density concentration (3,000 cells/well) in 96-well plates and incubated overnight in a 5% $CO_2$ incubator at 37° C. The cells were then treated with pure RITC labeled BSA (2.0 μg/mL) or PLGA-PC/fluorescence BSA/Lipid-PEG NP solution (10.0 ug/mL) for 4 h. A Zeiss AXIOVERT® 200 fluorescence/live cell imaging microscope was used to record the images.

Results

The results indicated that after four hours, large numbers of NPs entered the cells, and the loaded protein began to be released in a sustained fashion.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

We claim:

1. A method of making particles, comprising:
   (a) obtaining a copolymer dissolved in a first solvent to yield a dissolved copolymer, the copolymer comprising a polycation and a biodegradable polymer; and
   (b) generating particles from the dissolved copolymer, the particles comprising a cationic polymer core comprising the copolymer and an anionic active agent, wherein the particles comprise a zeta potential less than −10 mV.

2. The method of claim 1, wherein the anionic active agent comprises a therapeutic, prophylactic, or diagnostic agent.

3. The method of claim 1, wherein the anionic active agent comprises a protein or nucleic acid.

4. The method of claim 1, wherein the particles comprise a diameter between 10 nm and 200 nm.

5. The method of claim 1, wherein the particles comprise a zeta potential greater than −30 mV.

6. The method of claim 1, wherein the particles comprise the anionic active agent at an outside edge of the particle core.

7. The method of claim 1, wherein the particles are not aggregated.

8. The method of claim 1, wherein (a) comprises dissolving the copolymer in the first solvent to obtain a dissolved copolymer.

9. The method of claim 6, further comprising combining the dissolved copolymer with a second solvent having a different hydrophobicity than the first solvent to generate the particles.

10. The method of claim 9, wherein the second solvent is more hydrophobic than the first solvent.

11. The method of claim 9, further comprising forming an emulsion comprising the first solvent and the second solvent.

12. The method of claim 1, wherein the first solvent is a water immiscible solvent, and wherein generating the particles comprises combining the dissolved copolymer with an aqueous solution.

13. The method of claim 1, wherein generating the particles comprises flowing the dissolved copolymer through a microfluidic channel that-combines the dissolved copolymer with a copolymer non-solvent to form the particles.

14. The method of claim 1, wherein the particles have a homogeneous size distribution.

15. The method of claim 1, wherein the copolymer comprises three or more different polymer blocks.

16. The method of claim 1, wherein the copolymer comprises a conjugate selected from a targeting moiety, a lipid, a protective group, a reactive coupling group, a detectable label, or a therapeutic, prophylactic, or diagnostic agent.

17. The method of claim 1, wherein the copolymer is a polyalkylene oxide-modified copolymer.

18. The method of claim 1, wherein the first solvent comprises acetone, ethanol, methanol, isopropyl alcohol, acetonitrile or dimethyl sulfoxide.

* * * * *